United States Patent
Chu

(10) Patent No.: US 9,737,390 B2
(45) Date of Patent: Aug. 22, 2017

(54) MEDICAL ASSEMBLY FOR DELIVERING AN IMPLANT

(71) Applicant: Michael S. H. Chu, Brookline, MA (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 324 days.

(21) Appl. No.: 13/677,994

(22) Filed: Nov. 15, 2012

(65) Prior Publication Data

US 2013/0131441 A1 May 23, 2013

Related U.S. Application Data

(60) Provisional application No. 61/561,081, filed on Nov. 17, 2011.

(51) Int. Cl.
*A61F 2/02* (2006.01)
*A61F 2/00* (2006.01)
*A61B 17/06* (2006.01)
*A61B 17/00* (2006.01)

(52) U.S. Cl.
CPC ...... *A61F 2/0063* (2013.01); *A61B 17/06109* (2013.01); *A61F 2/0045* (2013.01); *A61B 2017/00477* (2013.01); *A61B 2017/00805* (2013.01); *A61B 2017/06042* (2013.01)

(58) Field of Classification Search
USPC ........................................................ 600/29
See application file for complete search history.

(56) References Cited

U.S. PATENT DOCUMENTS

| 2005/0043580 | A1* | 2/2005 | Watschke et al. ............... 600/30 |
| 2008/0082121 | A1* | 4/2008 | Chu .................... A61B 17/0625 606/205 |
| 2009/0171142 | A1* | 7/2009 | Chu .................... A61B 17/0401 600/37 |
| 2010/0268018 | A1* | 10/2010 | Chu ............................... 600/37 |
| 2011/0124956 | A1* | 5/2011 | Mujwid ................ A61F 2/0045 600/30 |

(Continued)

FOREIGN PATENT DOCUMENTS

WO 2005/048850 A2 6/2005

*Primary Examiner* — Christine H Matthews
*Assistant Examiner* — Shannon McBride
(74) *Attorney, Agent, or Firm* — Brake Hughes Bellermann LLP

(57) ABSTRACT

The present invention discloses a medical assembly including an elongate member having a proximal end portion and a distal end portion with a tapered tip. The tapered tip is configured to slide through a bodily tissue. The elongate member has a width referred to as a first width across at least a portion of the elongate member. The medical assembly further includes an implant having a first surface and a second surface. The implant is coupled to the elongate member such that a portion of the first surface of the implant is overlaid over a portion of the elongate member while the second surface faces opposite to the elongate member and is configured to contact the bodily tissue while being inserted. The implant has a width referred to as a second width such that the second width is smaller than the first width of the elongate member.

18 Claims, 28 Drawing Sheets

(56) References Cited

U.S. PATENT DOCUMENTS

2011/0144422 A1  6/2011 Chu
2012/0179175 A1* 7/2012 Hammell .............. A61F 2/0063
                                                606/151

* cited by examiner

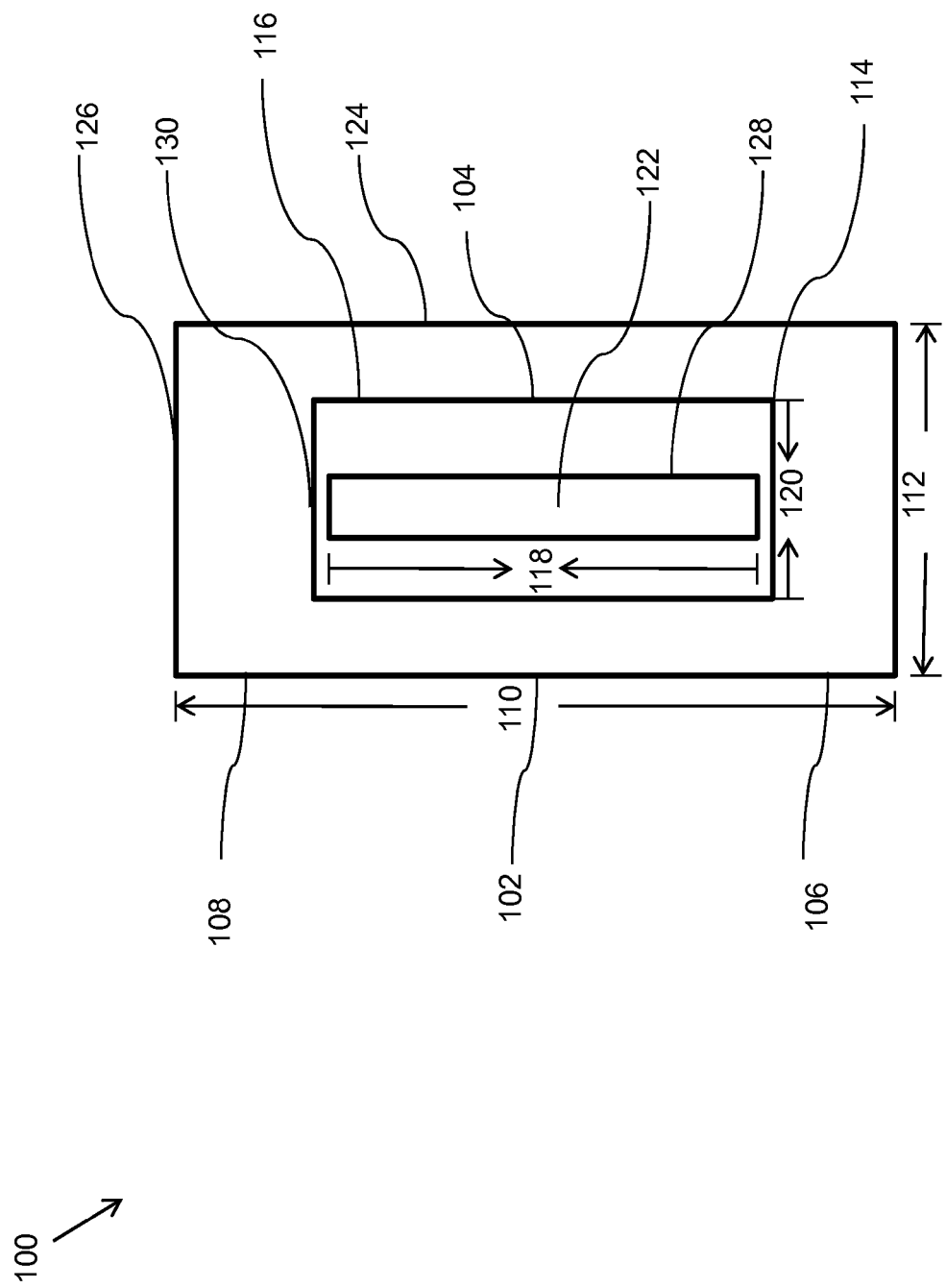

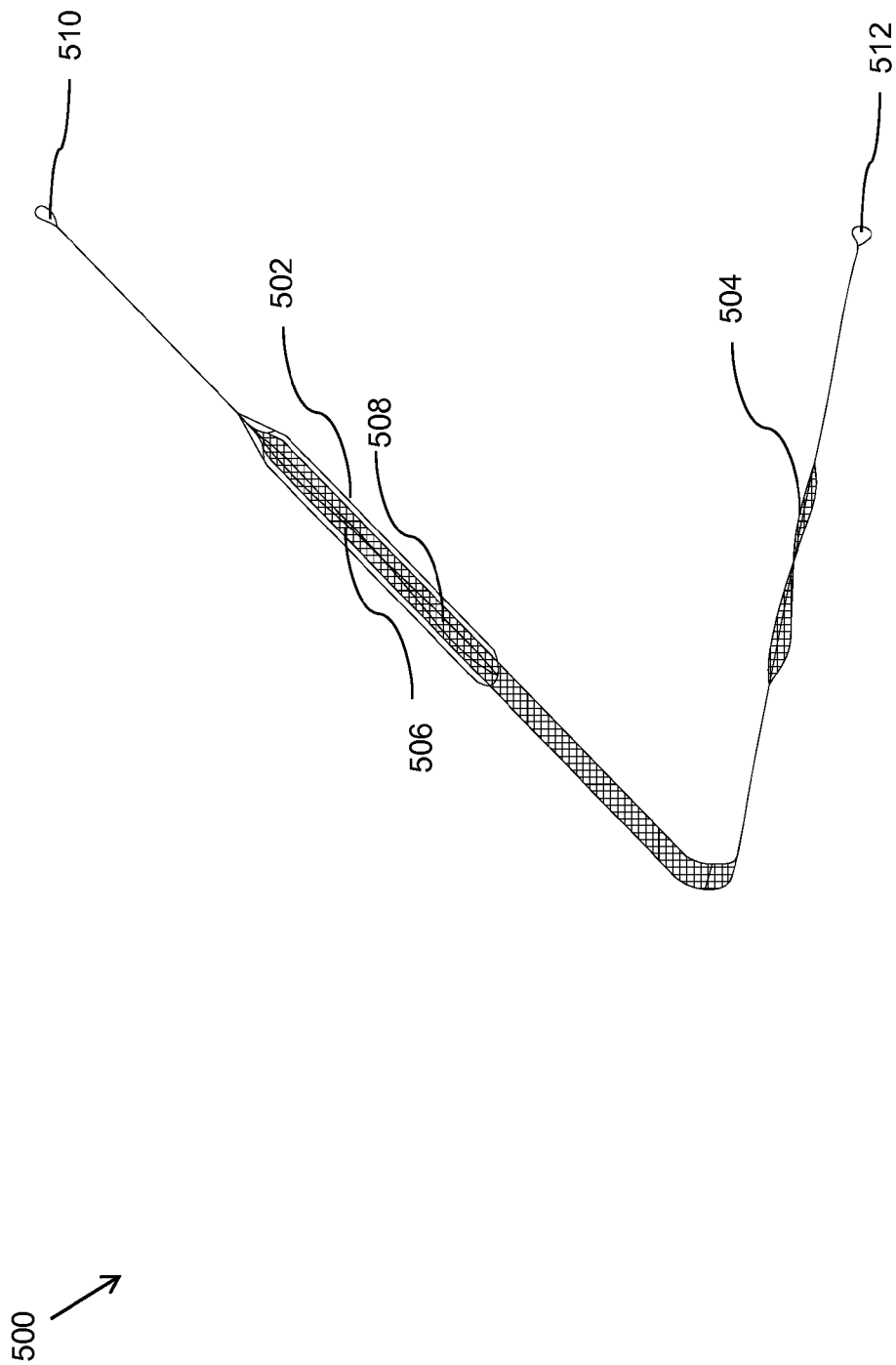

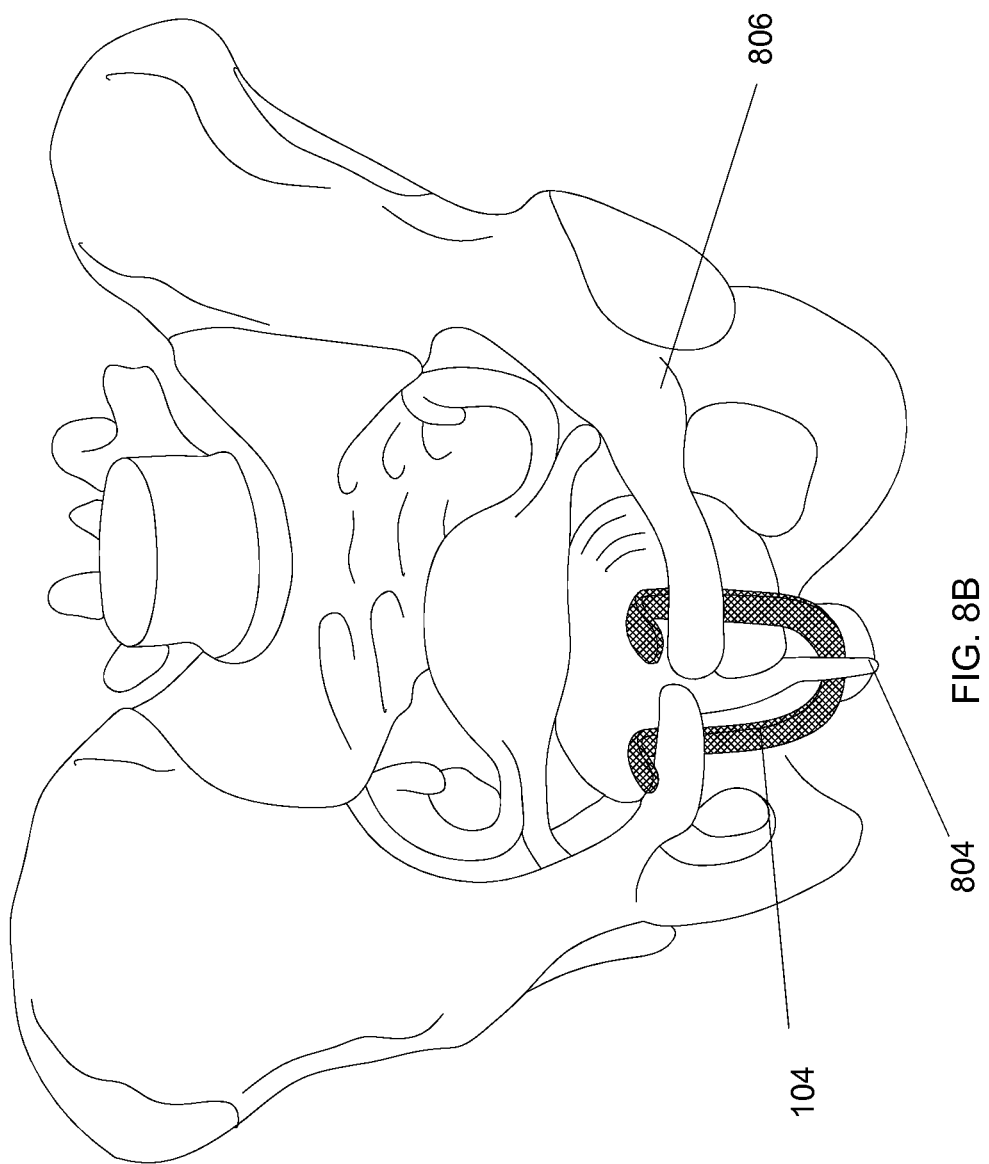

MEDICAL ASSEMBLY FOR DELIVERING AN IMPLANT

CROSS-REFERENCE TO RELATED APPLICATION

This application is a Nonprovisional of, and claims priority to, U.S. Patent Application No. 61/561,081, filed Nov. 17, 2011, entitled "A MEDICAL ASSEMBLY FOR DELIVERING AN IMPLANT", which is incorporated by reference herein in its entirety.

BACKGROUND

Field

The present invention generally relates to surgical devices and procedures, particularly to devices and methods for the delivery of implants within a patient's body.

Description of the Related Art

Pelvic health for men and women is a medical area of increasing importance. Examples of common pelvic ailments include incontinence (e.g. fecal and urinary), pelvic tissue prolapse (e.g. female vaginal prolapse), and other conditions of the pelvic floor.

A variety of treatment options are currently available to treat pelvic disorders. Some of these treatment options include external devices, behavioral therapy (such as biofeedback, electrical stimulation, or Kegal exercises), injectable materials, prosthetic devices and/or surgery.

One type of surgical procedure found to be an especially successful treatment option is an implant-based procedure. It involves placement of bodily implants under the bladder neck or the mid-urethra or any other location to provide a support platform. Placement of implants limits the endopelvis fascia drop.

The implants are delivered inside the patient's body using a delivery member that acts as a carrier and facilitate in delivery, placement and tension adjustment of the implant. Upon successful placement of the implant and appropriate tension adjustment, the delivery member is removed thereby letting the implant to stay inside the body. Several types of such delivery members and methods exist that assist in delivery of the implant inside a patient's body. These methods can involve complex procedures of delivery and placement of the implant. Further, the removal of these devices from the patient's body can be difficult.

In view of the above, there is a need of a method and a device that facilitate the delivery, and implantation or placement of the implant, and easy removal of the delivery member from the patient's body thus minimizing trauma.

SUMMARY

The present invention includes a medical assembly including an elongate member having a proximal end portion and a distal end portion with a tapered tip. The tapered tip is configured to slide through a bodily tissue. The elongate member has a width across at least a portion of the elongate member referred to as a first width. The medical assembly further includes an implant having a first side and a second side. The implant is coupled to the elongate member such that a portion of the first side of the implant is overlaid over a portion of the elongate member while the second side faces opposite the elongate member and is configured to contact the bodily tissue while being inserted. The implant has a width referred to as a second width such that the second width is smaller than the first width of the elongate member.

BRIEF DESCRIPTION OF THE FIGURES

The invention and the following detailed description of certain embodiments thereof may be understood with reference to the following figures:

FIG. 1 is a schematic diagram of a medical assembly, in accordance with some embodiments of the present invention.

FIGS. 5A and 5B are perspective views of a medical assembly, in accordance with an embodiment of the present invention.

FIGS. 8A-8C illustrate delivery of a medical assembly for placement of an implant in a patient's body opening, in accordance with an embodiment of the present invention.

DETAILED DESCRIPTION

Figure 2A:
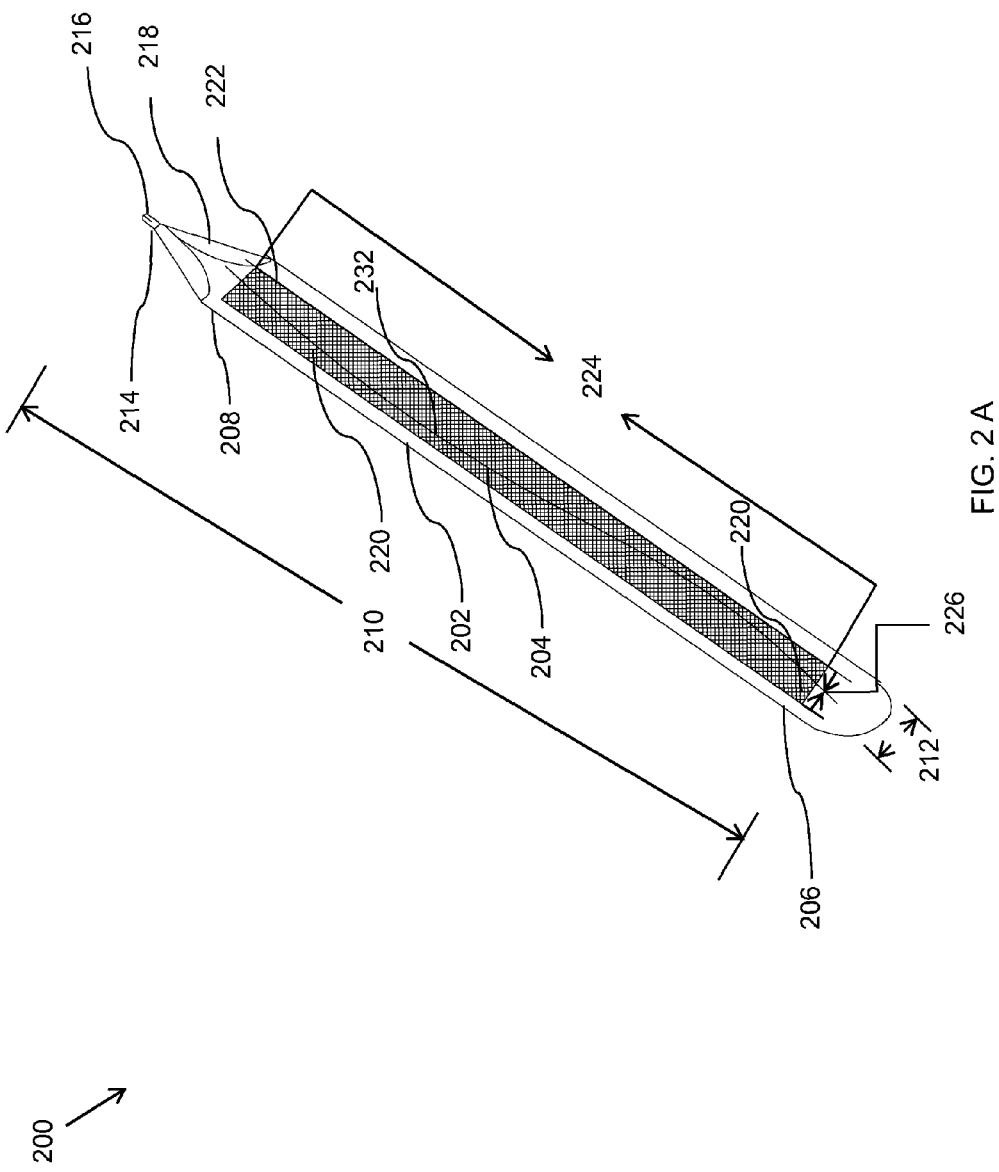
FIGS. 2A-2F are perspective views of a medical assembly, in accordance with an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition). The term "coupled" as used herein refers to any type of coupling although not necessarily a direct coupling. In other words, there may be intervening structure used to connect the coupled items. The term "directly coupled" as used herein refers to a direct coupling or a coupling that does not include any intervening structure.

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure of surgery through the patient's body orifice or incision as described in the present invention. The term proximal refers to an area that is closest to the operator. The term distal refers to an area that is farthest from the operator. The patient can be a male, a female or any other mammal.

FIG. 1 is a schematic diagram of a medical assembly 100, in accordance with some embodiments of the present invention. The medical assembly 100 includes an elongate member 102 and an implant 104. In some embodiments, the implant is configured to support bodily tissues for the treatment of pelvic floor disorders or other bodily tissues for the treatment of any other disorder.

The elongate member 102 includes a proximal end portion 106 and a distal end portion 108 with a length 110 of the elongate member 102 extending between the proximal end portion 106 and the distal end portion 108 longitudinally. In some embodiments, the length 110 of the elongate member 102 may be same across both longitudinal edges 124 of the elongate member 102. In other embodiments, the length 110 of the elongate member 102 can be different across the two longitudinal edges 124.

Further, the elongate member 102 includes a width 112 which is defined by a lateral extension 126 between two longitudinal edges 124 of the elongate member 102. In accordance with various embodiments, the elongate member 102 can have a variety of shapes such as rectangular, square, oval, trapezoidal, and the like.

In some embodiments, the proximal end portion 106 includes a single layer of material. In some embodiments, the single layer can be made of a multiple ply. In some embodiments, each ply can be of a different material. In some other embodiments, each ply may be of same material. For example, in some embodiments, the proximal end portion 106 does not define or include a lumen. In other words, in some embodiments, the proximal end portion 106 is devoid of a lumen or opening.

In some embodiments, the distal end portion 108 of the elongate member 102 has a tapered tip with a through lumen. In some other embodiments, the distal end portion 108 of the elongate member 102 has a tapered tip and does not include a through lumen.

The tapered tip is configured to slide through a bodily tissue and facilitate an insertion and movement through the patient's body. In some embodiments, the tapered tip includes folded edges of the distal end portion 108. In other embodiments, the tapered tip includes a taper-cut at the distal end portion 108.

In some embodiments, the lumen is formed by folded edges at the distal end portion 108 of the elongate member 102 such that the fold at the distal end portion 108 defines a tip with a through lumen. In other embodiments, the lumen is formed by a removable dilator coupled to the distal end portion 108 of the elongate member 102. In certain embodiments the dilator is insert-molded onto the taper-cut distal end portion 108 of the elongate member 102.

The implant 104 includes a proximal end portion 114 and a distal end portion 116 with a length 118 of the implant 104 extending between the proximal end portion 114 and the distal end portion 116 longitudinally. In some embodiments, the length 118 of the implant 104 may be same across both longitudinal edges 128 of the implant 104. In other embodiments, the length of the implant 104 can be different across the two longitudinal edges 128.

Further, the implant 104 includes a width 120 which is defined by a lateral extension 130 between two longitudinal edges 128 of the implant 104. In some embodiments, the width 120 of the implant 104 may be same across both lateral extensions 130. In other embodiments, the width 120 of the implant 104 can be different across the two lateral extensions 130. In accordance with various embodiments, the implant 104 can have a variety of shapes such as rectangular, square, trapezoidal, oval, and the like.

In some embodiments, the length 118 of the implant 104 is larger than the length 110 of the elongate member 102. In some embodiments, the length 118 of the implant is less than the length 110 of the elongate member 102. In some embodiments, the length 118 of the implant 104 is half of the length 110 of the elongate member 102. In other embodiments, the length 110 of the elongate member 102 and the length 118 of the implant 104 can be same. In some embodiments, the implant 102 is long enough to exit the skin incision. In some embodiments, the width 120 of the implant 104 referred hereafter to as a second width is less than the width 112 of the elongate member 102 referred hereafter to as a first width. In some other embodiments, the width of the elongate member can vary across its length. In such cases, the width of the elongate member across at least a portion of the elongate member is more than or greater than the width of the implant. The width of the elongate member across at least the portion can be referred to as the first width in such cases.

The implant 104 further includes two planar horizontal surfaces—a first surface and a second surface that are separate by a thickness of the implant 104. The first surface and the second surface are on opposite sides such that they face away from one another when viewed in a horizontally lying plane or a vertically upright location.

In some embodiments, the implant 104 can include a detanged section (without tangs) at its proximal end portion 114 to avoid mesh irritation and erosion upon placement of the implant within the body such as underneath the urethra. The length of the detanged section can vary based on surgical requirements. The detanged section can be extended towards distal end portion 116 to prevent stretch and unraveling of the implant 104. The distal end portion 116 is preferred to be tanged to allow the tangs to engage the surrounding tissue to secure the implant 104 in place. In other embodiments, anchors, barns and the like elements are added to the implant 104 to secure it into place.

In some embodiments, the elongate member 102 and/or the implant 104 are made of a synthetic material such as polymeric material and the like. In some embodiments, the single layer can be made of a multiple ply. In some embodiments, each ply can be of a different material. In other embodiments, each ply can be of the same material. In some embodiments, the implant 104 includes a polymeric mesh body. In other embodiments, the implant 104 includes a polymeric planar body without mesh cells and structures. Exemplary polymeric materials are polypropylene, polyester, polyethylene, nylon, PVC, polystyrene, and the like. In some embodiments, the elongate member 102 and/or the implant 104 are made of a non-woven polymeric material. In some embodiments, the surface of the elongate member 102 and/or the implant 104 are smooth to avoid or reduce irritation on adjacent body tissues during medical interactions. Additionally, in some embodiments, the elongate member 102 and/or the implant 104 are not stretchable but flexible to adapt movements along the anatomy of the human body and reduce suture pullout. In some embodiments, the attributes such as softness, lightness, conformity and strength are required in the elongate member 102 and/or the implant 104 for efficient tissue repair and implantation. Furthermore, in some embodiments, softness, lightness, conformity, and strength are certain other attributes required in the elongate member 102 and/or the implant 104 for efficient tissue repair and implantation. In some other embodiments, the elongate member 102 and/or the implant 104 can be made of natural materials such as biologic material or a cadaveric tissue and the like.

The implant 104 is configured to be coupled to the elongate member 102 through a coupling member 122 that couples both the elongate member 102 and the implant 104. In some embodiments, the implant 104 is directly coupled to the elongate member 102, such as via an adhesive. In other embodiments, the implant 104 is coupled to the elongate member 102 via a coupling member 122 or a coupling mechanism. In some embodiments, the implant 104 is coupled to an outer surface of the elongate member 102. In other words, in some embodiments, the implant is coupled to a portion of the elongate member 102 that is devoid of a lumen or is coupled to the elongate member 102 outside of or away from any lumen defined by the elongate member 102.

In certain embodiments, the coupling member 122 releaseably couples the elongate member 102 to the implant 104. In some embodiments, a portion of the coupling member 122, implant 104, or elongate member 102 may be severed or cut to release the elongate member 102 from the implant 104. In some other embodiments, the coupling member 122 is not releasable. The implant is coupled to the elongate member 102 such that a portion of the first surface of the implant 104 is overlaid over a portion of the elongate member 102 and it makes contact with the elongate member 102 thereat. The second surface facing opposite to the first surface is open to interact with the bodily tissue and does not make any contact with the elongate member 102.

In accordance with some embodiments, the coupling member 122 is at least one selected from the group consisting of a thread, a tack, a skewer, a knot, a tuck and a tie. In accordance with some embodiments, the thread can be a suture. The thread may be made of biological materials and/or synthetic materials. The thread may be strong enough to hold both the elongate member 102 and implant 104 securely. In some embodiments, the thread is monofilament. In other embodiments, the thread is multifilament. In some embodiments, the thread can be referred to as leader. The leader may be colored for visualization during cystoscopy.

In accordance with some embodiments, only one implant is coupled to the elongate member as described above. In certain other embodiments, more than elongate member similar to the elongate member 102 can be coupled to the implant 104. For example, two elongate members similar to the elongate member 102 can be coupled to the implant 104 in such a way that a first portion of the implant 104 is coupled to a first elongate member and a second portion of the implant 104 is coupled to a second elongate member. In some embodiments, the implant 104 can further be made up of a support member and multiple arms extending outward from the support member that are configured to be placed at different locations inside the patient's body. In accordance with these embodiments, each of the arms of the implant 104 may also be configured to be coupled to a separate elongate member similar to the elongate member 102.

The implant 104 is configured to be placed over and coupled to the elongate member 102 in such a manner that the 124 edges of the elongate member 104 extend beyond the longitudinal edges 128 of the implant 102 along a lateral direction. For example, in accordance with some embodiments, the implant 104 is centered along the width 110 of the elongate member 102 thus preventing the tangs along the edge of the implant 104 from engaging the bodily tissues. While the elongate member 102 is still coupled after being inserted into the patient's body, the implant 104 can be adjusted in either direction, thereby adjusting the tension of the implant 104 during placement.

FIGS. 2A and 2B are perspective views of a medical assembly 200 in accordance with an embodiment of the present invention. The medical assembly 200 includes an elongate member 202 and an implant 204.

The elongate member 202 includes a proximal end portion 206 and a distal end portion 208 with a length 210 of the elongate member 202 extending between the proximal end portion 206 and the distal end portion 208 longitudinally. In accordance with the illustrated embodiment of FIG. 2A, the length 210 of the elongate member is same across both longitudinal edges 234 of the elongate member 202. In other embodiments, however, the length 210 of the elongate member 202 can be different across the two longitudinal edges 234. Further, the elongate member 202 includes a width 212 which is defined by a lateral extension 236 between two longitudinal edges 234 of the elongate member 202.

In some embodiments, the distal end portion 208 of the elongate member 202 has a tapered tip 214 with a through lumen 216. The tapered tip 214 is configured to slide through a bodily tissue and facilitate an insertion and movement through the patient's body. For example, the tapered tip 214 can be used to assist in the delivery of the implant 204 to a pelvic region or other bodily location. The tapered tip 214 of the elongate member 202 is tapered from a larger width and/or diameter at a proximal or trailing end to a smaller width and/or diameter at a distal or leading end of the tapered tip 214. The tapered tip 214 of the elongate member 202 is configured to produce a passage through a tissue to facilitate implant placement. Using a tapered portion to introduce the implant 204 into the pelvic region can help reduce handling or pulling of the implant 204 itself, thereby reducing or eliminating potential damage to the implant 204. In accordance with the illustrated embodiment, the tapered tip 214 includes folded edges 218 of the distal end portion 208.

In some embodiments, as shown in FIG. 2A, the lumen 216 is formed by folded edges 218 at the distal end portion 208 of the elongate member 202 such that the fold at the distal end portion 208 defines a tip 214 with a through lumen 216 thereat.

Figure 2:
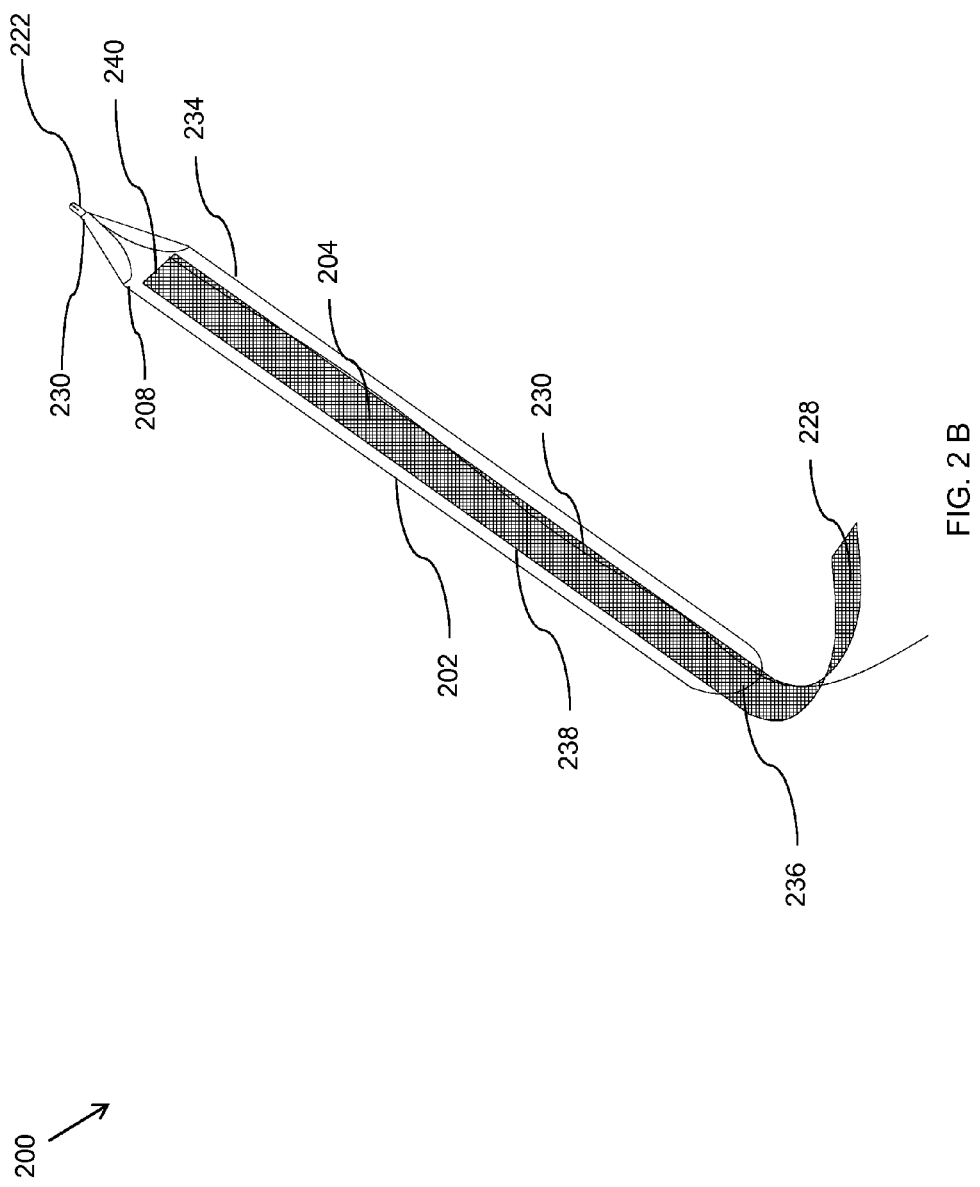

The implant 204 includes a proximal end portion 220 and a distal end portion 222 with a length 224 of the implant 204 extending between the proximal end portion 220 and the distal end portion 222 longitudinally. In accordance with the embodiment illustrated in FIG. 2, the length 224 of the implant 204 is same across both longitudinal edges 238 of the implant 204. In other embodiments, however, the length 224 of the implant 204 can be different across the two longitudinal edges 238.

Further, the implant 204 includes a width 226 which is defined by a lateral extension 240 between two longitudinal edges 238 of the implant 204. In accordance with the embodiment illustrated in FIG. 2A, the width 226 of the implant 204 is same across both lateral extensions 240. In other embodiments, the width 226 of the implant 204 can be different across the two lateral extensions 240. In accordance with various embodiments, the implant 204 can have a variety of shapes such as rectangular, square, trapezoidal, and the like.

In some embodiments, as shown in FIG. 2A, the length 224 of the implant 204 is less than the length 210 of the elongate member 202. For example, the length 224 of the implant 204 can be half of the length 210 of the elongate member 202. In some other embodiments, the length 224 of the implant 204 can be larger than the length 210 of the elongate member 202. In still other embodiments, the length 210 of the elongate member 202 and the length 224 of the implant 204 can be same. In some embodiments, the width 226 of the implant 204 referred hereafter to as a second width is lesser than the width 212 of the elongate member 202 referred hereafter to as a first width.

In accordance with various embodiments, the implant 204 further includes two planar horizontal surfaces—a first surface 228 and a second surface 230 that are separate by the thickness of the implant 204 and each facing opposite one another when viewed in a horizontally lying or vertically upright plane.

In some embodiments, the elongate member 202 and the implant 204 are made of a synthetic material such as polymeric material and the like. In some embodiments, the implant 204 includes a polymeric mesh body. Various types of materials that can be utilized in the manufacture of the elongate member 202 and the implant 204 have been described above in conjunction with FIG. 1.

The implant 204 is configured to be coupled to the elongate member 202 through a coupling member 232 that couples both the elongate member 202 and the implant 204. In certain embodiments, the coupling member 122 releasably couples the elongate member 102 to the implant 104. In some other embodiments, the coupling member 122 is not releasable. The implant 204 is coupled to the elongate member 202 such that a portion of the first surface 228 of the implant 204 is overlaid over a portion of the elongate member 202 and that makes a contact with the elongate member 202. The second surface 230 facing opposite the elongate member 202 is open to interact with the bodily tissue and does not make any contact with the elongate member 202. As shown in FIG. 2A, the coupling member 232 is a thread extending at least across the length of the implant 204 and coupling the implant 204 with the elongate member 202 at either discrete locations or in a continuous pattern.

Figure 2C:
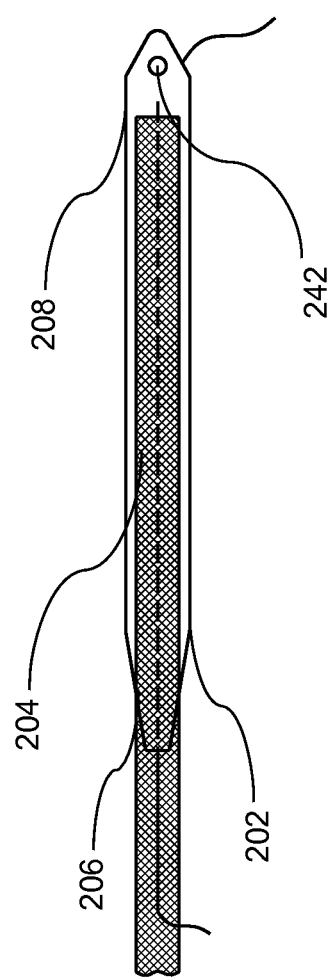

In accordance with the above embodiment illustrated in FIGS. 2A and 2B, the lumen 216 is provided at the distal end portion of the elongate member 202. However, in certain other cases, the elongate member 202 includes a hole or opening 242 at the distal end portion 208 instead of the lumen 216 such as shown in FIG. 2C. The hole 242 is configured to associate the elongate member 202 to the delivery device through an L shape slot such as shown later in FIG. 7B. As shown, the proximal end portion 206 of the elongate member 202 is tapered in accordance with the embodiment shown in FIG. 2C. In still other embodiments, both the end portions—distal end portion 208 and the proximal end portion 206 of the elongate member 202 may be tapered. The tapered ends are configured to adjust the implant 204 in both directions through tissues. For example, the tapered ends may facilitate movement of the implant 204 in either direction within the body of the patient. In yet other embodiments, none of the end portions are tapered. Referring to the FIG. 2C further, the coupling member 232 is stitched in and out and across at least some portion of the elongate member 202 and the implant 204 linearly. The coupling can be done through stitches at either discrete locations or in a continuous pattern. The amount of stitches is preferred to be minimal to allow easy removal of the coupling member 122 but enough to maintain the association of the elongated member 202 and the implant 204. In some embodiments, the proximal end portion 206 of the elongate member 202 is stitched thereby preventing the elongate member 202 from engaging surrounding tissues as the implant 204 is adjusted.

In some embodiments, end portions of the coupling member 122 such as a thread end portions are set free at the proximal and the distal end portion of the elongate member 202. In yet another embodiment, the end portions of the coupling member 122 can be secured to the elongate member 202 and/or the implant 204, In some embodiments, as show in FIG. 2D, the elongate member 202 has different widths across the length 210 of the elongate member 202 such that at least some portion of the elongate member 202 has a narrower width than the width 226 of the implant 204. In some embodiments, the portion with the narrower width allows for minimally invasive cystoscopy before the wider trailing portion of the implant 204 is pulled into place.

In some embodiments, a flap 244 may be attached to the elongate member 202 at its distal end portion 208 and is configured to protect the distal end portion 222 (leading edge) of the implant 204 from engaging with surrounding tissues as shown in FIG. 2E. FIG. 2E illustrates a top view of the implant 204 and the elongate member 202 with a flap 244 attached through a tack or heat seal. FIG. 2F is the side view of the assembly shown in FIG. 2E. The flap 244 is essentially a kind of cover that extends from the elongate member. Specifically, in the illustrated embodiment, the flap is attached at its one end portion over the elongate member 202 while its other end portion is free to move up and down with respect to the elongate member 202 such that the implant distal portion 222 can pass through and inside the volume covered by the free end of the flap 244. In this manner, the implant leading edge or the distal end portion 222 can be prevented from engaging with the surrounding tissues. Also, center tabs, center lines, anchors, barbs or the like elements can be added to the implant to aid in securing the implant to a tissue. Other association means to a delivery device can be adapted such as a Capio dart for the association to the Capio suturing device.

Figure 3A:
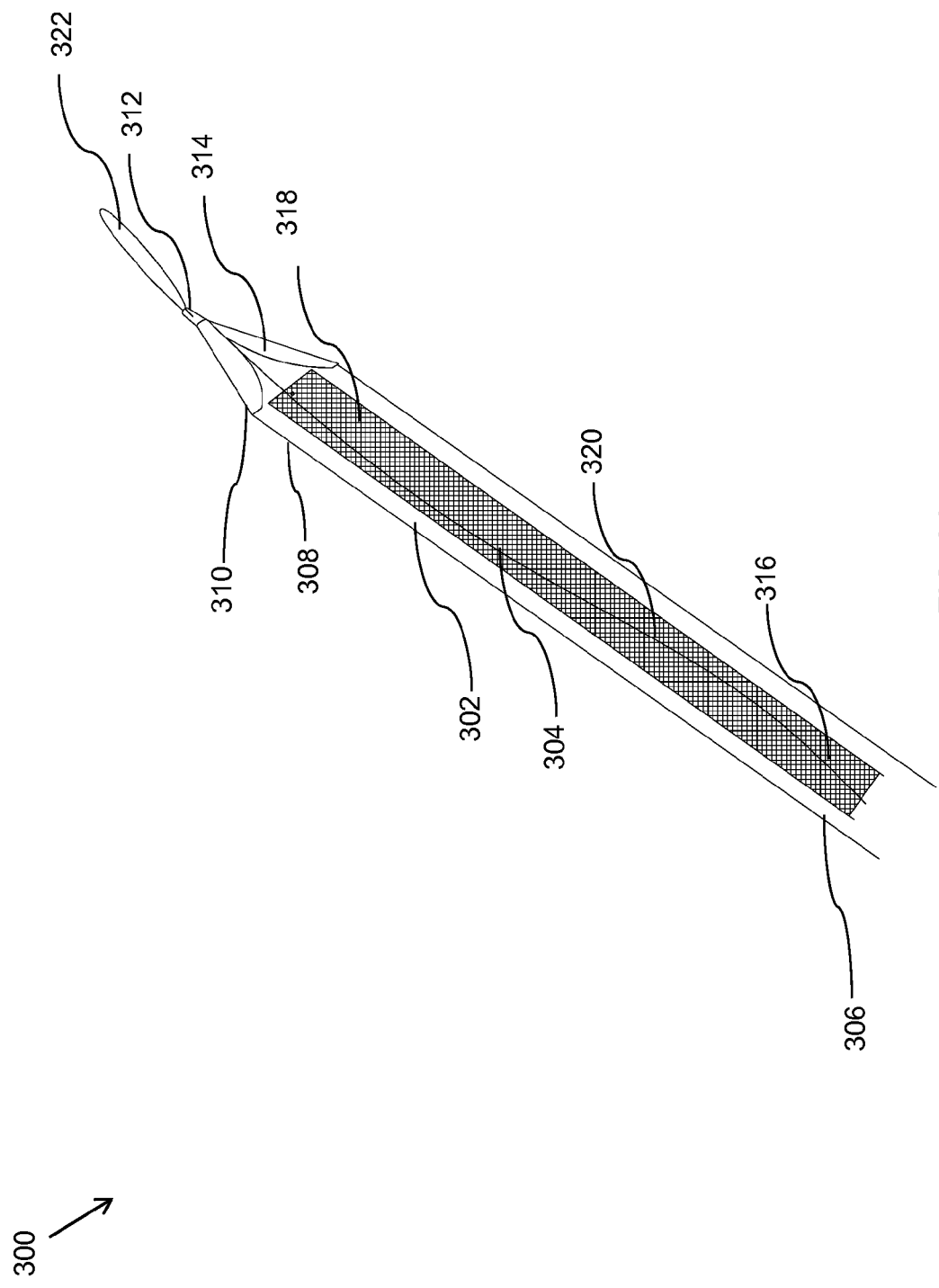
FIGS. 3A and 3B are perspective views of a medical assembly, in accordance with an embodiment of the present invention.

FIG. 3A is a perspective view of a medical assembly 300 in accordance with an embodiment of the present invention. The medical assembly 300 includes an elongate member 302 and an implant 304. The elongate member 302 includes a proximal end portion 306 and a distal end portion 308 with a length of the elongate member 302 extending between the proximal end portion 306 and the distal end portion 308 longitudinally. Further, the elongate member 302 includes a width referred to as a first width. The distal end portion 308 of the elongate member 302 has a tapered tip 310 with a through lumen 312. In some embodiments, as shown in FIG. 3A, the lumen 312 is formed by folded edges 314 at the distal end portion 308 of the elongate member 302.

The implant 304 includes a proximal end portion 316 and a distal end portion 318 with a length of the implant 304 extending between the proximal end portion 316 and the distal end portion 318 longitudinally. Further, the implant 304 includes a width referred to as a second width such that the second width is lesser than the first width.

The implant 304 further includes two planar horizontal surfaces—a first surface and a second surface each facing opposite one another. The implant 304 is configured to be coupled to the elongate member 302 through a coupling member 320 such that a portion of the first surface of the implant 304 is overlaid over a portion of the elongate member 302 and makes a contact with the elongate member 302. The second surface facing opposite the elongate member 302 is open to interact with the bodily tissue and does not make any contact with the elongate member 302.

The medical assembly 300 further includes a loop 322 provided at the distal end portion 308 of the elongate member 302. In some embodiments, the loop 322 can be a thread or a suture. The loop 322 is configured to form a connection between a delivery device and the lumen 312. In some other embodiments, there can be a hole instead of the lumen at the distal end portion of the elongate member 302 as has been described above. In such cases, the elongate member 302 is wrapped around the implant 304 and the coupling member 320 and heat sealed together to close any opening or lumen thereat (if any). In some embodiments, the delivery device can be a conventionally used delivery device such as a surgical needle device. In accordance with various embodiments, the delivery device can include a slot configured to receive a portion of the loop 322 such that the delivery device can be associated with the loop 322 through the slot. In some embodiments, the slot can be of any shape such as an L, T, reversed L, angled slot, and the like.

In some embodiments, the loop 322 can extend along a portion of the elongate member 302 and the implant 304 to form the coupling member 320 configured to couple at least a portion of the implant 304 with the elongate member 302. The coupling member 320 in this embodiment is a thread or a suture. The thread is threaded in and out of the elongate member 302 and the implant 304 such that it keeps them intact. In accordance with some other embodiments, the loop 322 and the coupling member 320 may not be integral parts of the same thread. The coupling member 320 and the loop 322 can be discrete elements and formed of separate threads.

Figure 3B:
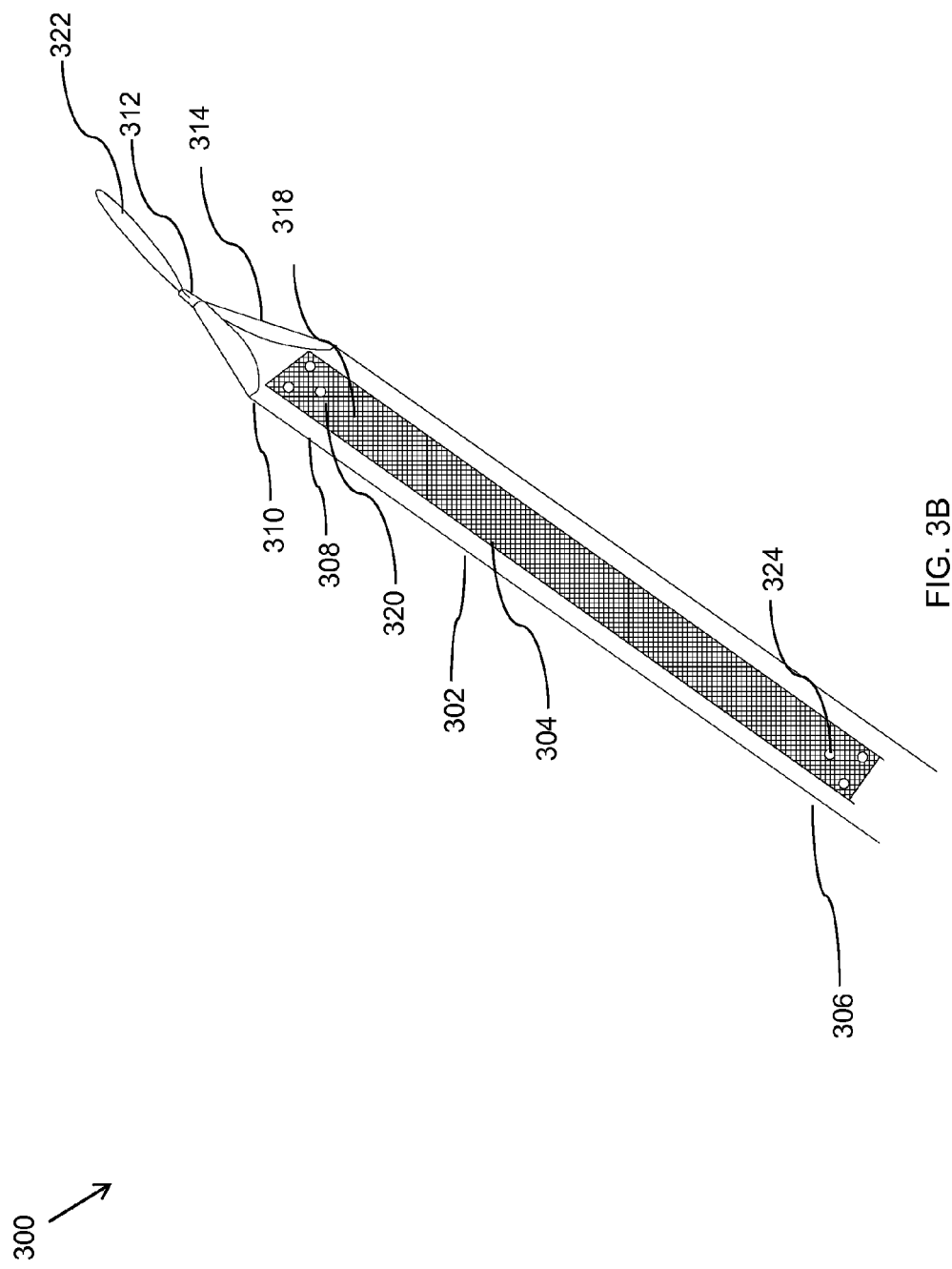

In accordance with the embodiment illustrated in FIG. 3A, the thread is used as the coupling member 320. In some other embodiments the coupling member 320 can be a tack or a plurality of tacks as shown in FIG. 3B. The tacks are small areas in which the polymer implant 304 such as a polypropylene mesh implant is melted to the polymer elongate member 302 to form an association. The tacks can be shaped as small circles (as shown in FIG. 3B as 324) or can be a straight line across a portion of the width of the implant 304. The tacks can have any preferred shape and/or with orientation such as chevron shape. Tacks are configured to be broken by pulling the elongate member 302 and the implant 304 in opposite directions or apart. The tacks may include any kind of nails, staples or any other fastener configured to couple the elongate member 302 with the implant 304. In accordance with various embodiments, there may be one or more tacks along an overlapping length of the implant 304 over the elongate member 302.

Figure 4A:
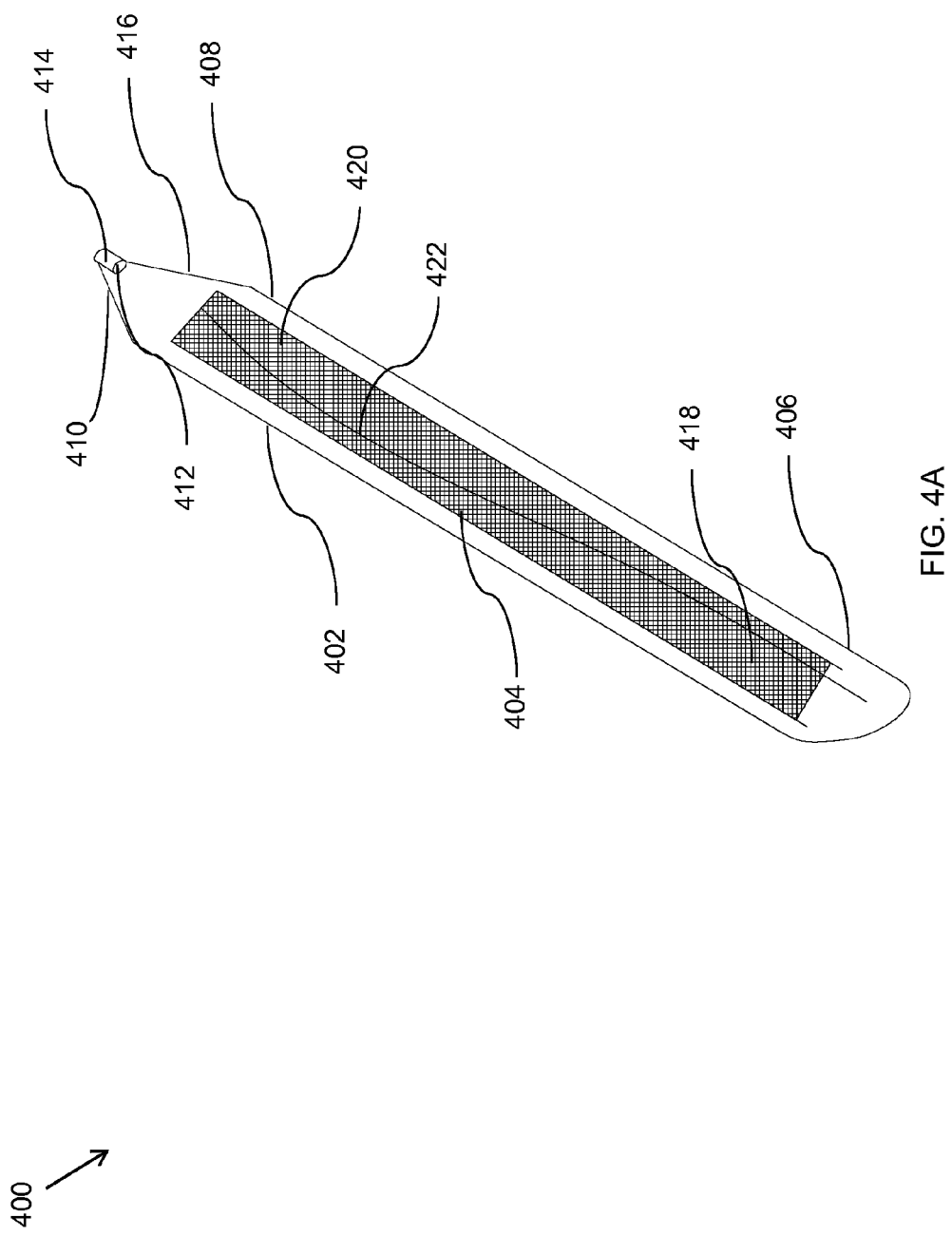
FIGS. 4A and 4B are perspective views of a medical assembly, in accordance with an embodiment of the present invention.

FIG. 4A is a perspective view of a medical assembly 400 in accordance with an embodiment of the present invention. The medical assembly 400 includes an elongate member 402 and an implant 404. The elongate member 402 includes a proximal end portion 406 and a distal end portion 408 with a length of the elongate member 402 extending between the proximal end portion 406 and the distal end portion 408 longitudinally. Further, the elongate member 402 includes a width referred to as a first width. The distal end portion 408 of the elongate member 402 has a tapered tip 410 with a through lumen 412. In some embodiments, as shown in FIG. 4A, the lumen 412 is formed by a removable dilator 414 coupled to the distal end portion 408 of the elongate member 402. The lumen 412 is integrally formed into the dilator 414. For example, the dilator 414 with the through lumen 412 is insert molded onto the distal end portion 408 of the elongate member 402. In this embodiment, the tip 410 includes a taper-cut 416 at the distal end portion 408 and the dilator 414 with the through lumen 412 is coupled thereat. In some embodiments, the dilator 414 is removably coupled to the elongate member 402. In other embodiments, the dilator 414 is fixedly coupled to the elongate member 402.

In some embodiments, the dilator 414 has a tapered shape at its tip such that it is configured to dilate or expand an opening or a passage within a bodily tissue. In other embodiments, the dilator 414 can be a thin shaped tubular member without a taper but configured to dilate the tissue because of its thin and sharp nature. The dilator 414 is configured to be attached to a delivery device. In some embodiments, the delivery device can be a conventionally used delivery device such as a surgical needle device. In some embodiments, the dilator 414 can be sized to accept a step needle delivery device (as shown later in FIG. 7C) such as the Solyx™ delivery device as sold by Boston Scientific Corporation, or the dilator 414 can be sized and lengthened to be fitted to an Advantage™ delivery device as sold by Boston Scientific Corporation. In certain embodiments, the dilator 414 can be sized or lengthened to be fitted to an Advantage™ delivery device. The implant 404 includes a proximal end portion 418 and a distal end portion 420 with a length of the implant 404 extending between the proximal end portion 418 and the distal end portion 420 longitudinally. Further, the implant 404 includes a width referred to as a second width such that the second width is less than the first width.

The implant 404 further includes two planar horizontal surfaces—a first surface and a second surface each facing opposite one another. The implant 404 is configured to be coupled to the elongate member 402 through a coupling member 422 such that a portion of the first surface of the implant 404 is overlaid over a portion of the elongate member 402 and makes a contact with the elongate member 402. The second surface facing opposite the elongate member 402 is open to interact with the bodily tissue and does not make any contact with the elongate member 402.

Figure 4B:
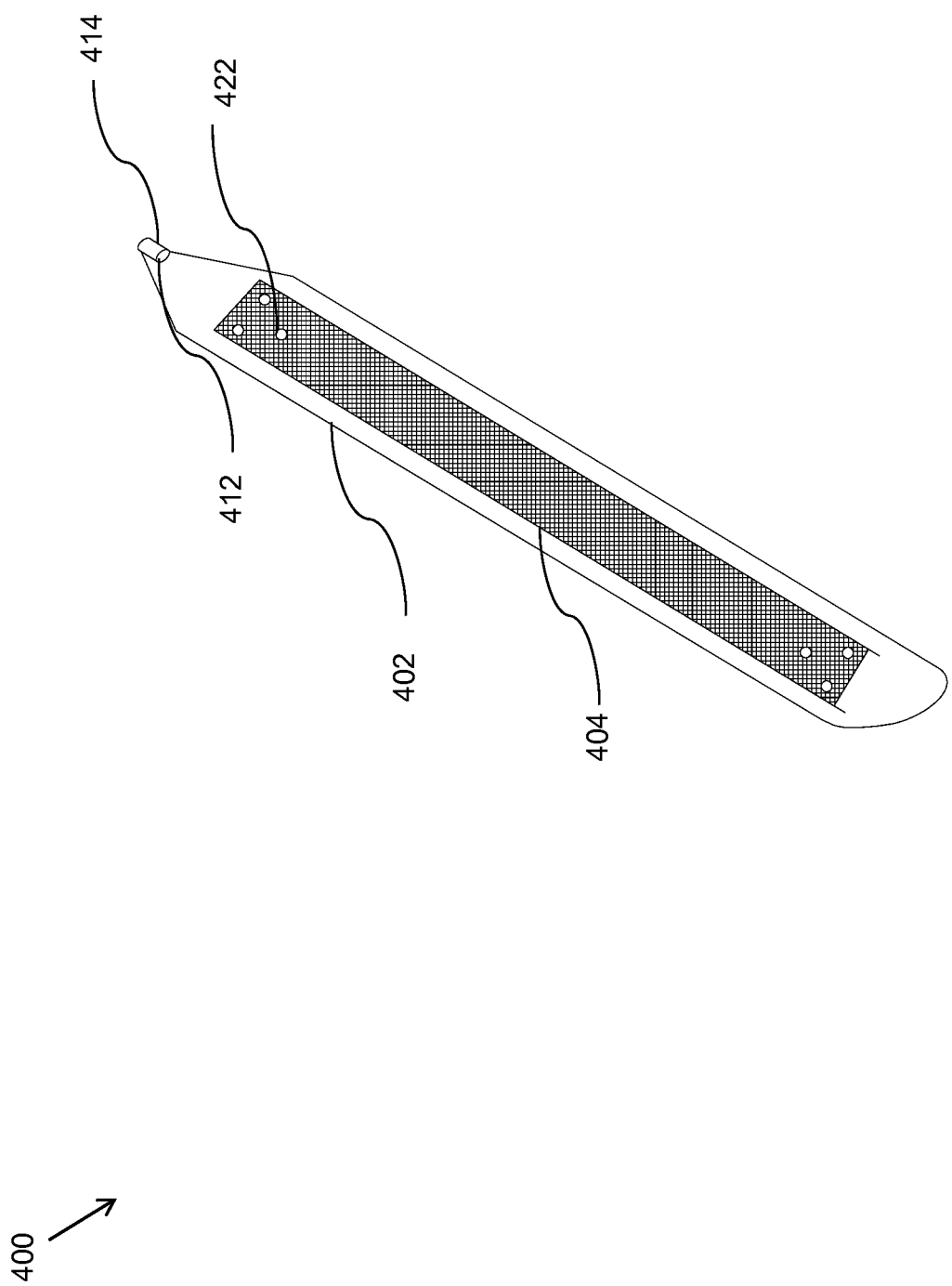

In accordance with the embodiment illustrated in FIG. 4A, the thread is used as the coupling member 422. In some other embodiments the coupling member 422 can be a tack or a plurality of tacks as shown in FIG. 4B.

FIG. 5A is a perspective view of a medical assembly 500 in accordance with an embodiment of the present invention. The medical assembly 500 includes a first elongate member 502, a second elongate member 504, and an implant 506. The first elongate member 502 and the second elongate member 504 can be similar to the elongate members described in conjunction with various figures above. Similarly, the implant 506 can be similar to the implants described in conjunction with various figures above. In some embodiments, a first portion of the implant 506 is coupled to the first elongate member 502 and a second portion of the implant 504 is coupled to the second elongate member 504. The coupling can be done using a coupling member 508. The coupling member has been described in conjunction with various figures above.

FIG. 5A illustrates the use of a first loop 510 and a second loop 512 coupled to the first elongate member 502 and the second elongate member 504 respectively. However, it must be appreciated that in some other embodiments, dilators similar to the dilator described above in conjunction with various figures can be employed instead of loops 510 and 512. In some embodiments, the dilator is preferred to be of a different color such as blue to aid in visualization during cystoscopy in an incontinence procedure.

In accordance with this embodiment, the respective faces of the elongate members 302 and 304 can be facing each other or opposing each other. The first loop 510 and the second loop 512 can be used to associate the medical assembly 500 to a delivery device with "L" shaped slot such as the Lynx™ or Obtryx™ by Boston Scientific Corporation (shown later in FIG. 7B).

Figure 5B:
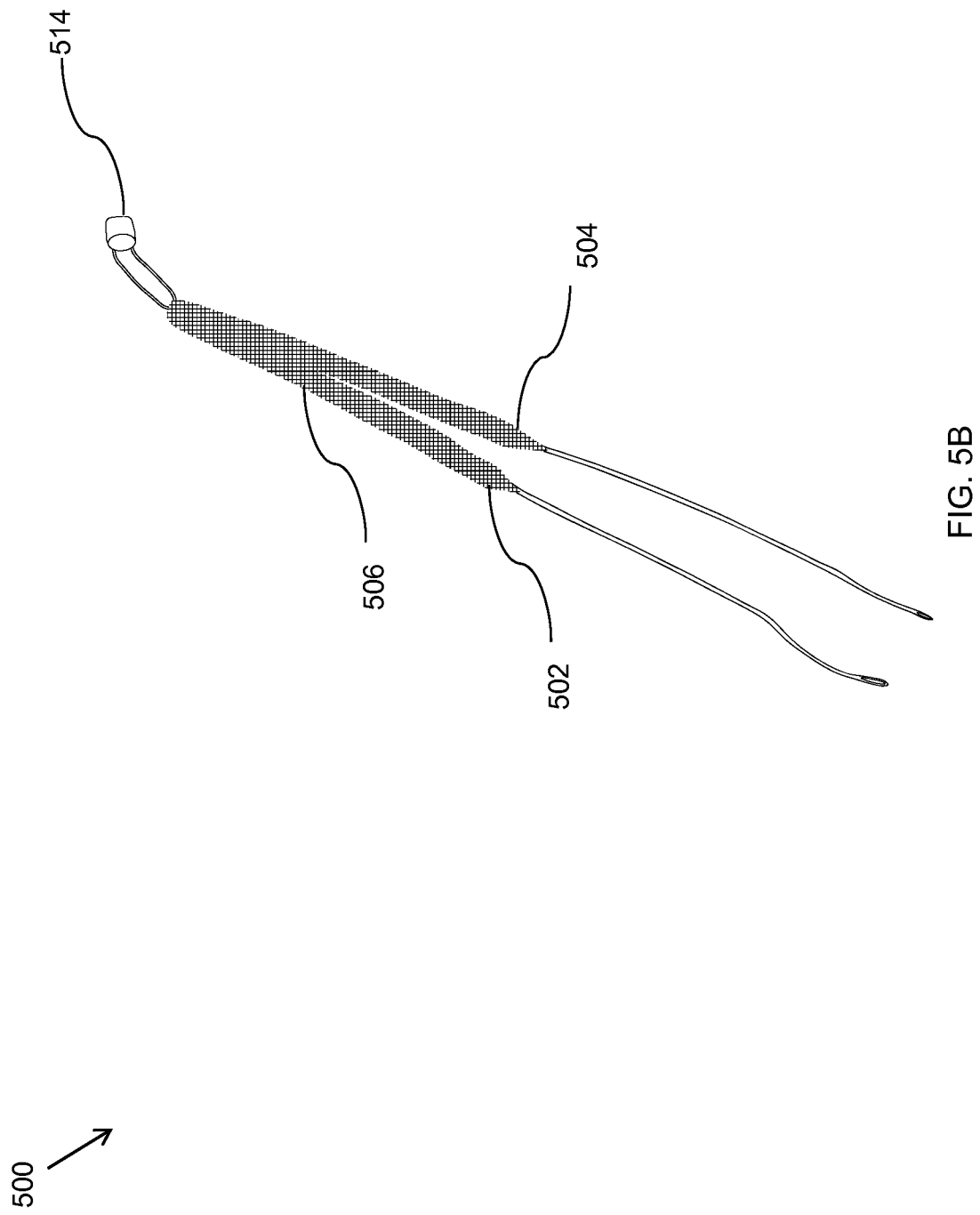

In some embodiments, the medical assembly 500 may further include a center tab 514 configured to locate center of the implant 506 as shown in FIG. 5B. The center tab 514 is configured to assist in placement of the implant 506 during surgery and helps a surgeon to identify the center of the implant 506. The center tab 514 further facilitates in providing substantially equal distribution of the implant 506 on each side of a target bodily portion during surgery. In some embodiments, the center tab 514 can be pulled to adjust the tension or location of the implant 506

Several types of coupling patterns may be employed in various embodiments to couple the elongate member with the implant such as those described below in conjunction with FIGS. 6A-6F without limitations.

FIGS. 1-5B shows various embodiments of the medical assembly wherein various types of coupling arrangement are provided to secure the implant onto the elongate member. In addition, there can be several other types of coupling members and the pattern of coupling. A few exemplary coupling members and the patterns of coupling the implant with the elongate member are further described below in conjunction with FIGS. 6A-6H.

Figure 6A:
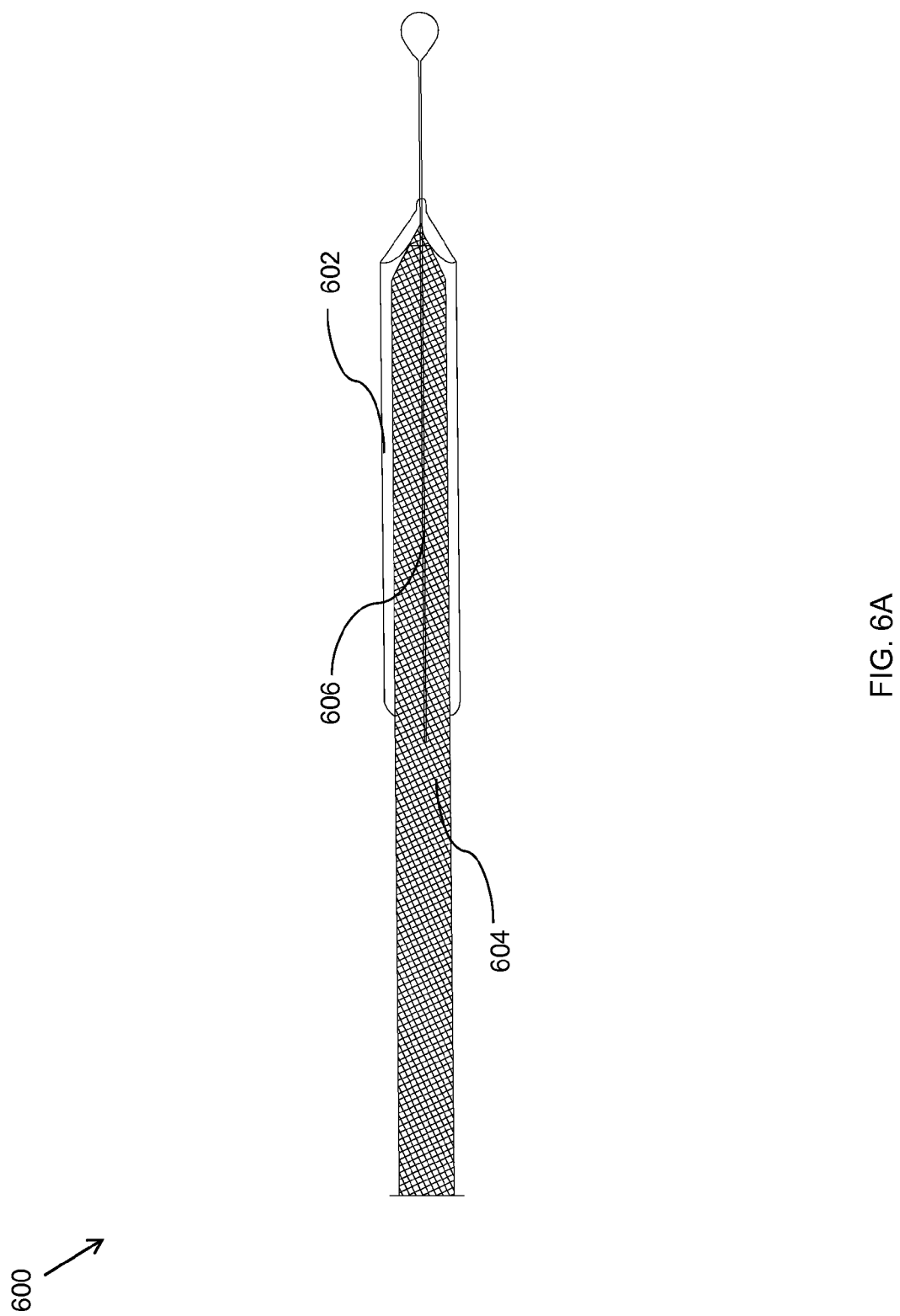
FIGS. 6A-6H illustrate exemplary coupling members and patterns of coupling an implant to an elongate member, in accordance with several embodiment of the present invention.

FIG. 6A shows coupling of the elongate member 602 with the implant 604 through the coupling member 606 that is designed in the form of a thread. In some embodiments, the thread is tied by stitching in and out across at least some portion of the elongate member 602 and the implant 604 linearly. The coupling can be done through stitches at either discrete locations or in a continuous pattern.

Figure 6B:
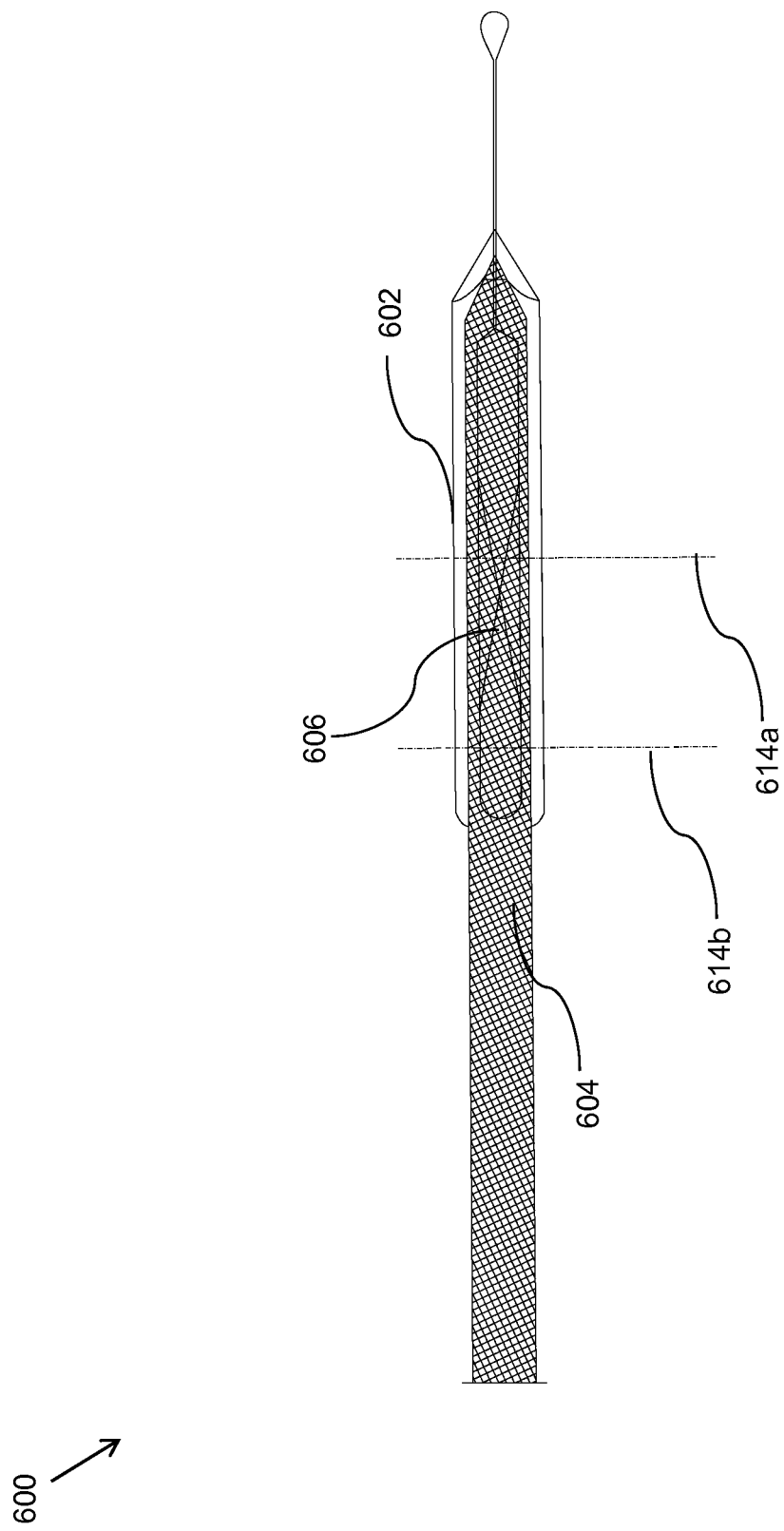
Figure 6C:
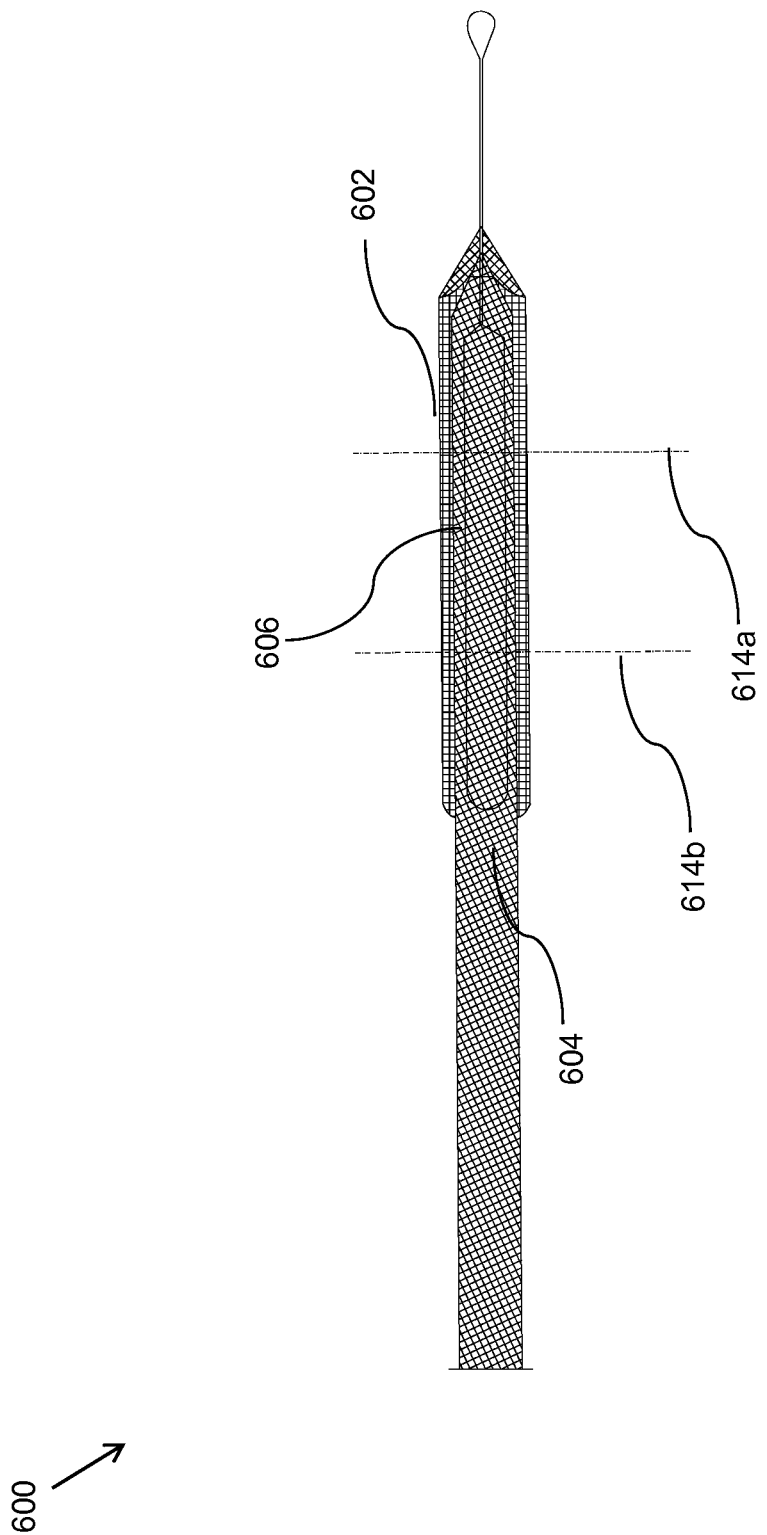
Figure 6D:
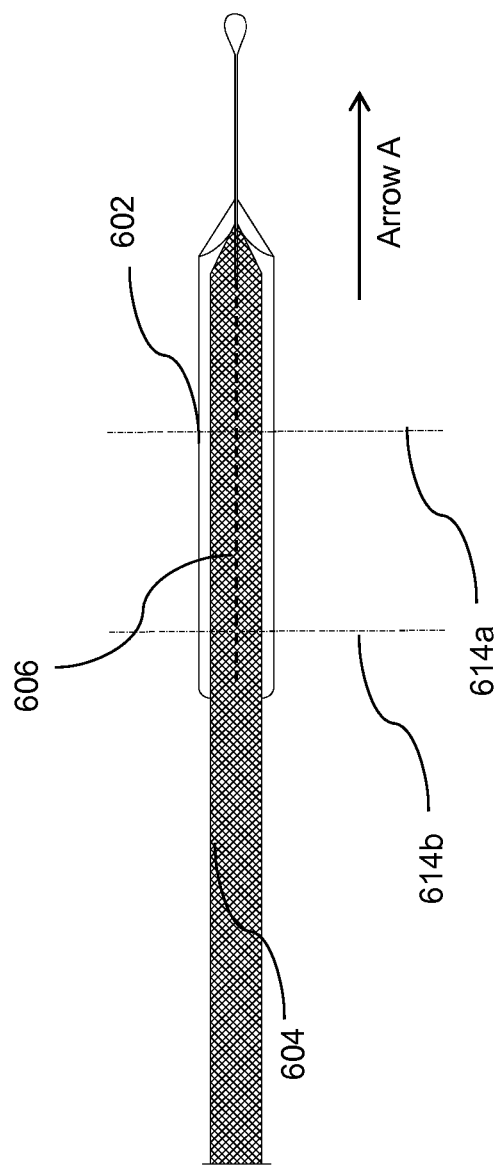

FIG. 6B shows that the coupling member 606 is associated to the implant 604 and the elongate member 602 on X-Y plane i.e. in and out of the implant 604 in "figure 8" pattern. In some embodiments, the coupling member 606 can be configured on X-Y plane i.e. in and out of the implant 604 in an oval loop pattern as shown in FIG. 6C. In other embodiments, the coupling member 606 can be configured in an oval loop or "figure 8" pattern on X-Z plane of the implant 604 as shown in FIG. 6D. Referring to FIG. 6D, the dotted lines 614a and 614b as shown indicate tissue and skin levels in the patient's body respectively. The tissue and skin levels determine the length of the elongate member 602 and the implant 604 inside the patient's body. In some embodiments, the decoupling of the coupling member 606 can be done by cutting the coupling member 606 from outside the skin level 614b. Once the coupling member 606 is cut, the elongate member 602 is pulled in the direction of arrow A as shown in FIG. 6D. One of the cut coupling member 606 ends will travel back toward the body and follow the path of its pattern to reverse its direction to come out of the body attached to the elongated member 602. In some embodiments, the lumen is closed off to secure the thread to the elongate member.

Figure 6E:
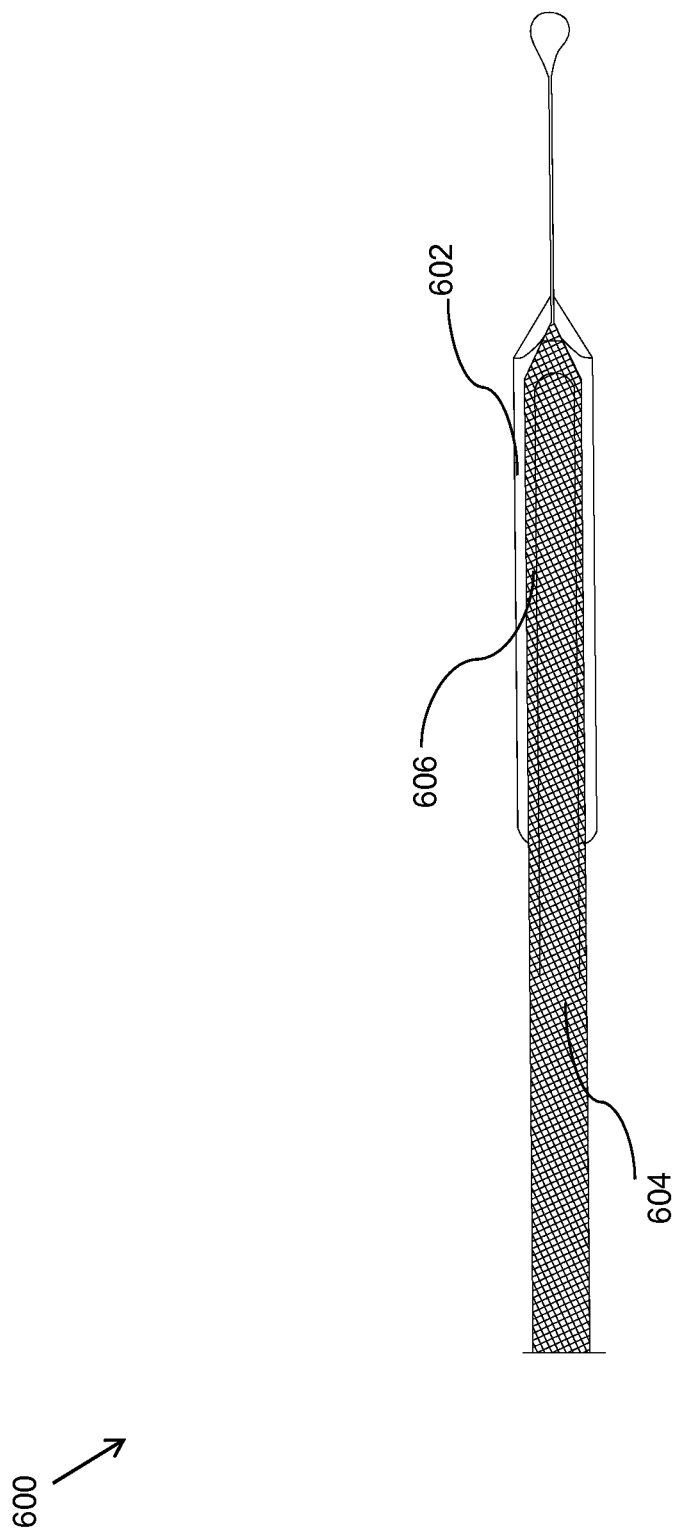

FIG. 6E shows that the coupling member 606 is threaded in and out of the second side of the elongate member 602 and the implant 604 in an upside down U pattern.

Figure 6F:
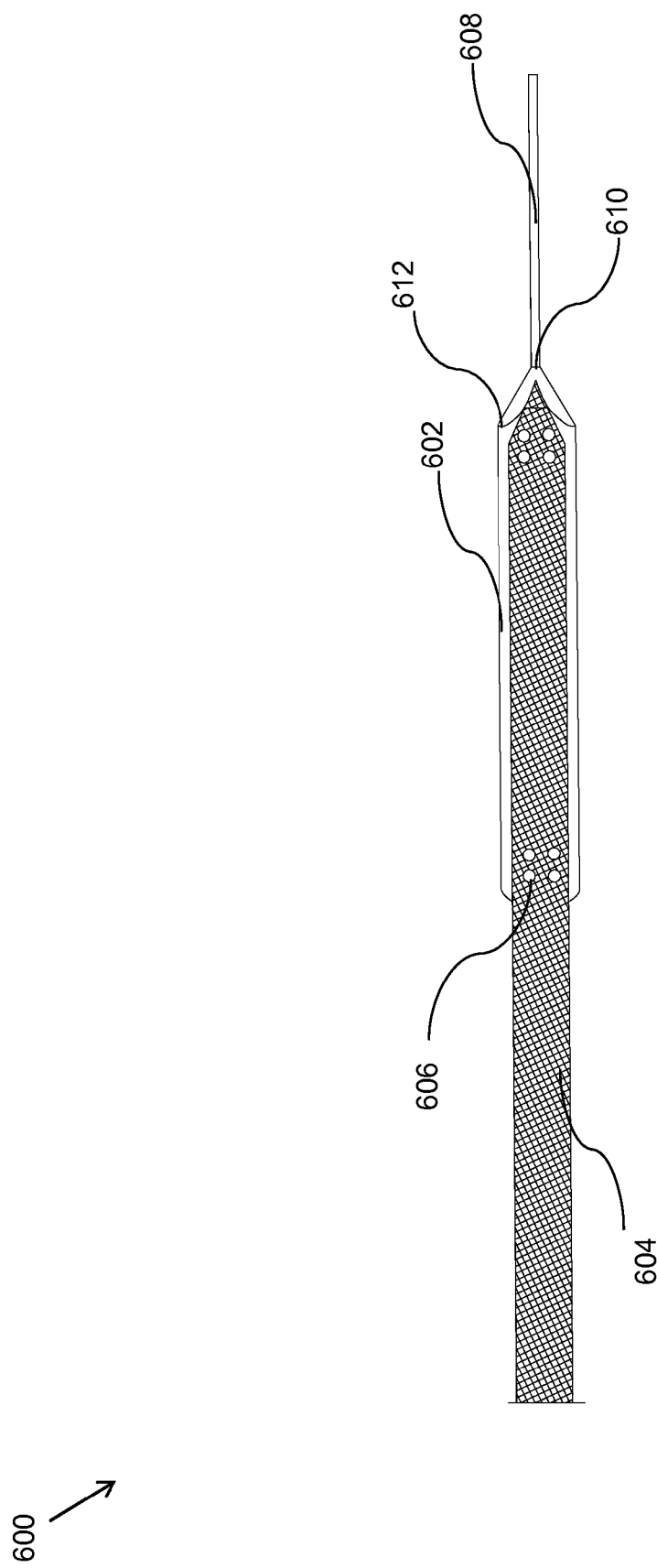

FIG. 6F shows that the elongate member 602 is associated to the implant 604 solely by tacks. Any external surgical tube can also be attached at a lumen 610 of a tapered tip 612 of the elongate member 602 providing a connection between a delivery device such as a surgical needle and the elongate member 602. In some embodiments, the surgical tube 608 may be sized to fit the BSC Advantage™ delivery device or the advantage Fit ™ delivery device. The tube 608 can aid in untwisting the implant 604 assembly as well as aid visually in cystoscopy.

Figure 6G:
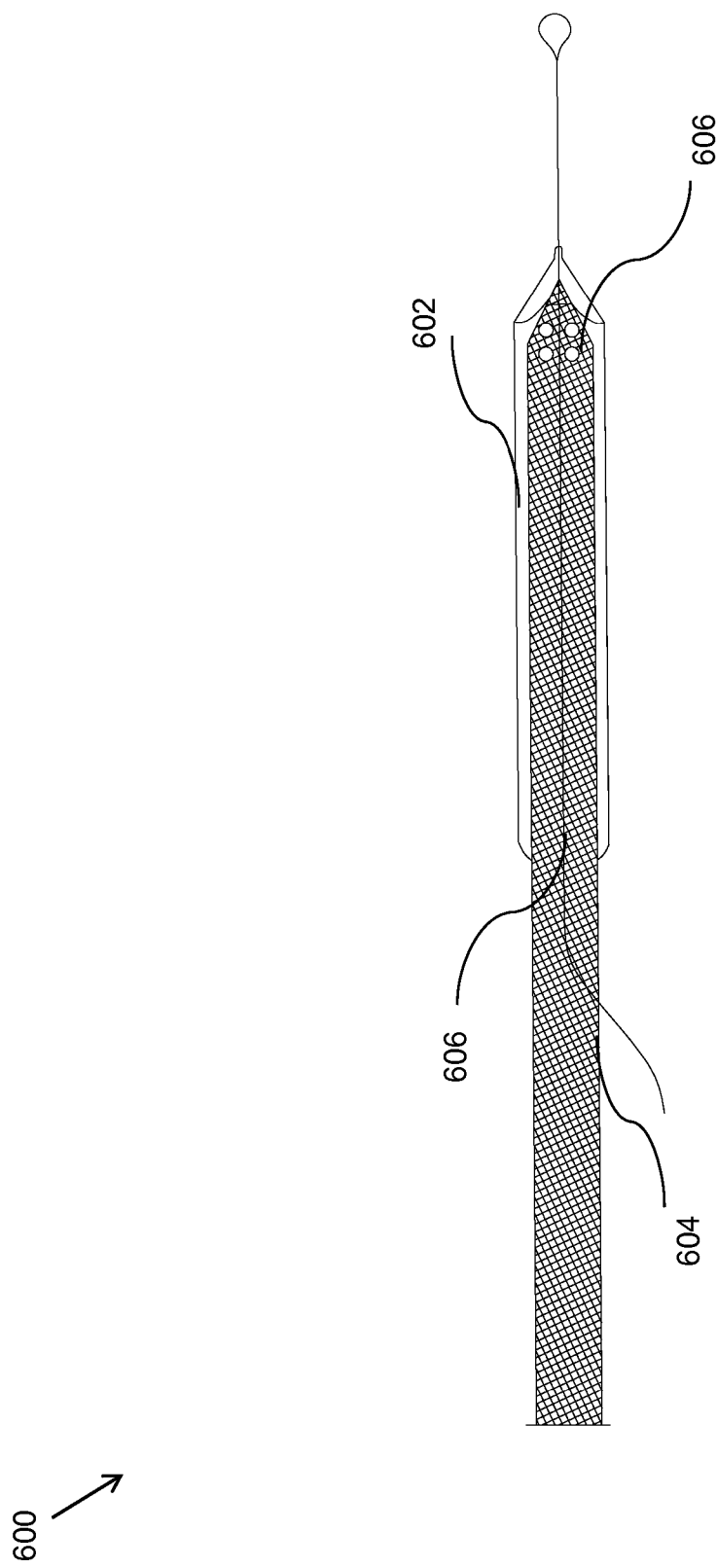

FIG. 6G shows that the coupling member 606 includes a thread as well as tacks for coupling the implant 604 with the elongate member 602.

Figure 6H:
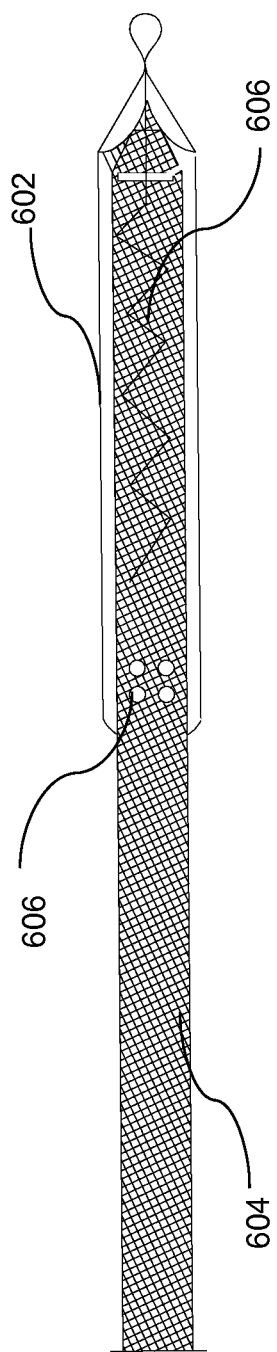

FIG. 6H shows the coupling member 606 with a zigzag pattern of the thread along with tacks to associate the second surface of the elongate member 602 to the implant 604.

Figure 7A:
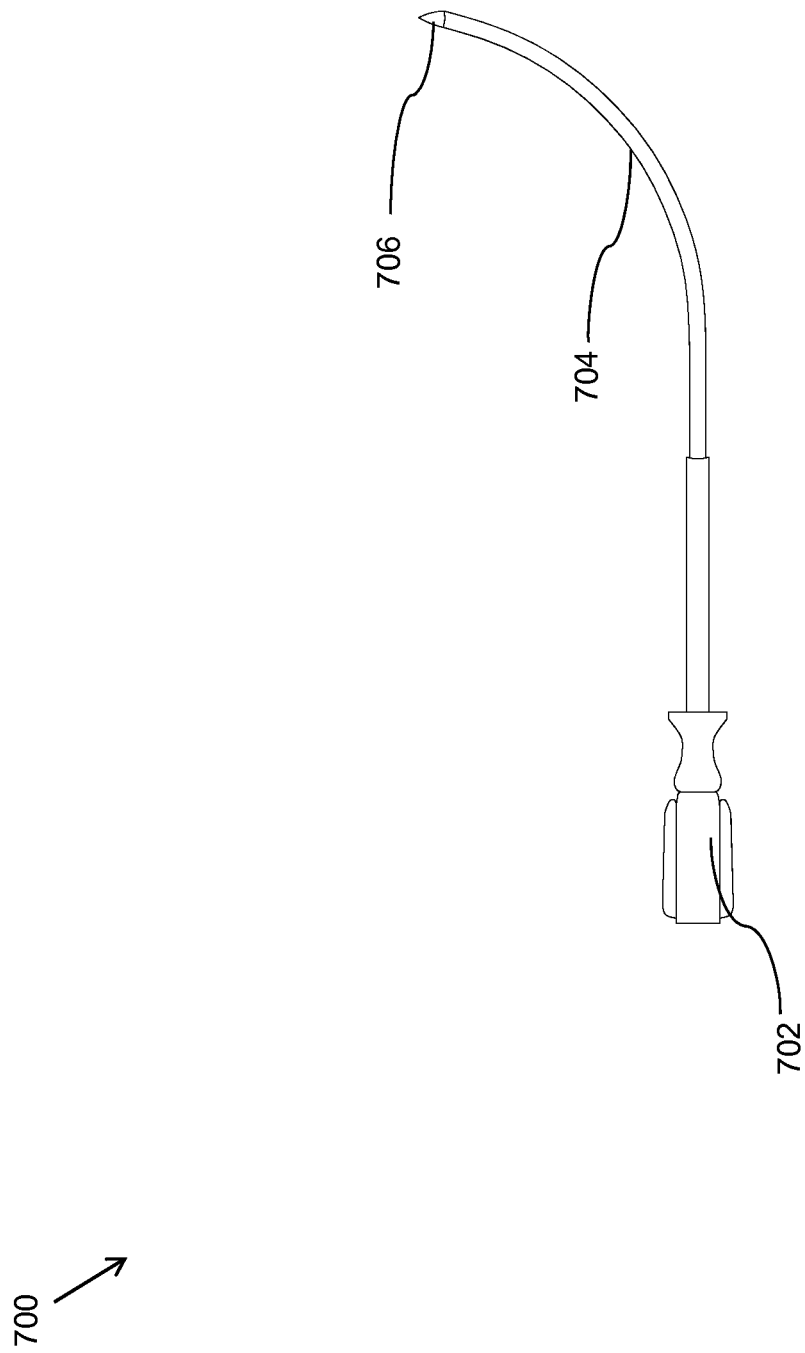
FIGS. 7A-7C illustrate a delivery device, in accordance with an embodiment of the present invention.
Figure 7B:
Figure 7C:
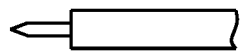

In accordance with various embodiments, the delivery device used in the abovementioned description can be any conventional surgical needle. An exemplary delivery device 700 is shown in FIGS. 7A-7C. In some embodiment, as shown in FIG. 7A, the delivery device 700 includes a handle 702 and a needle 704. The needle 702 further has a needle tip 706. FIG. 7B shows an L shaped slot and FIG. 7C depicts a step needle.

Figure 8A:
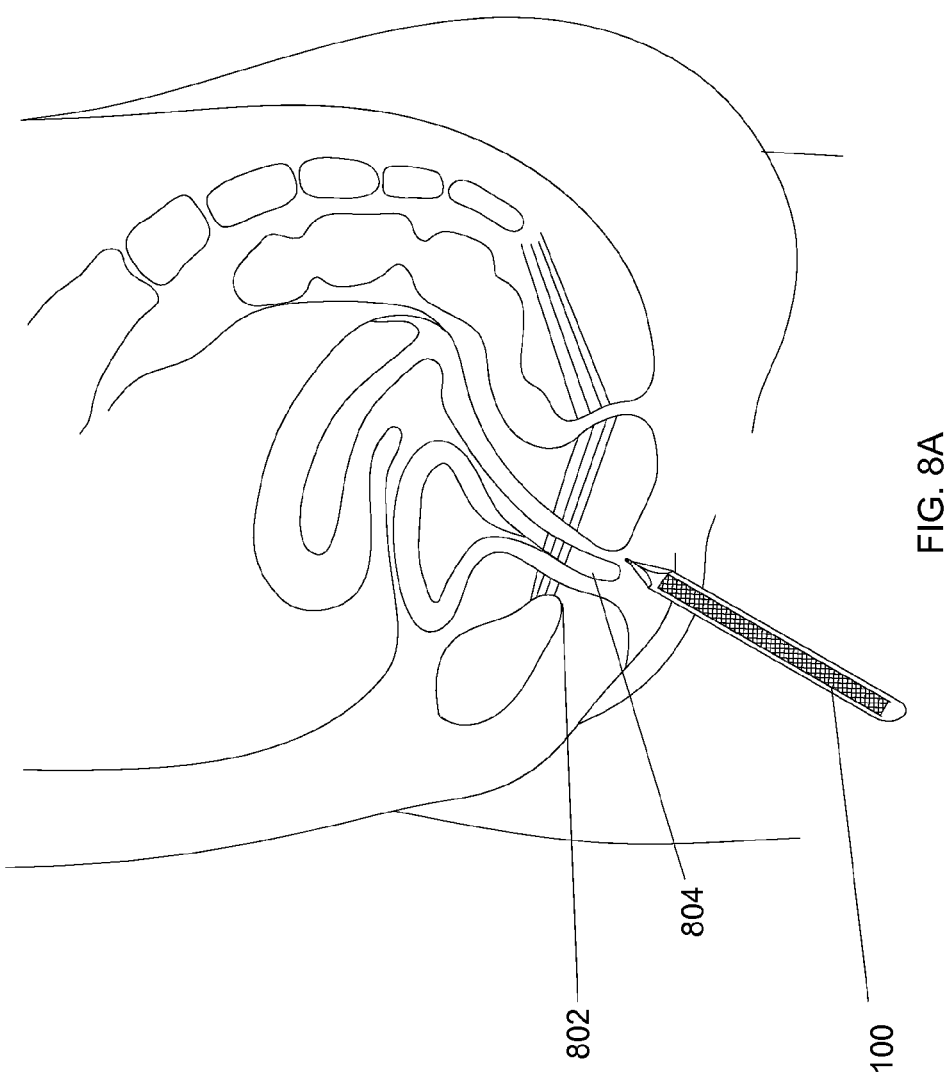
Figure 8C:
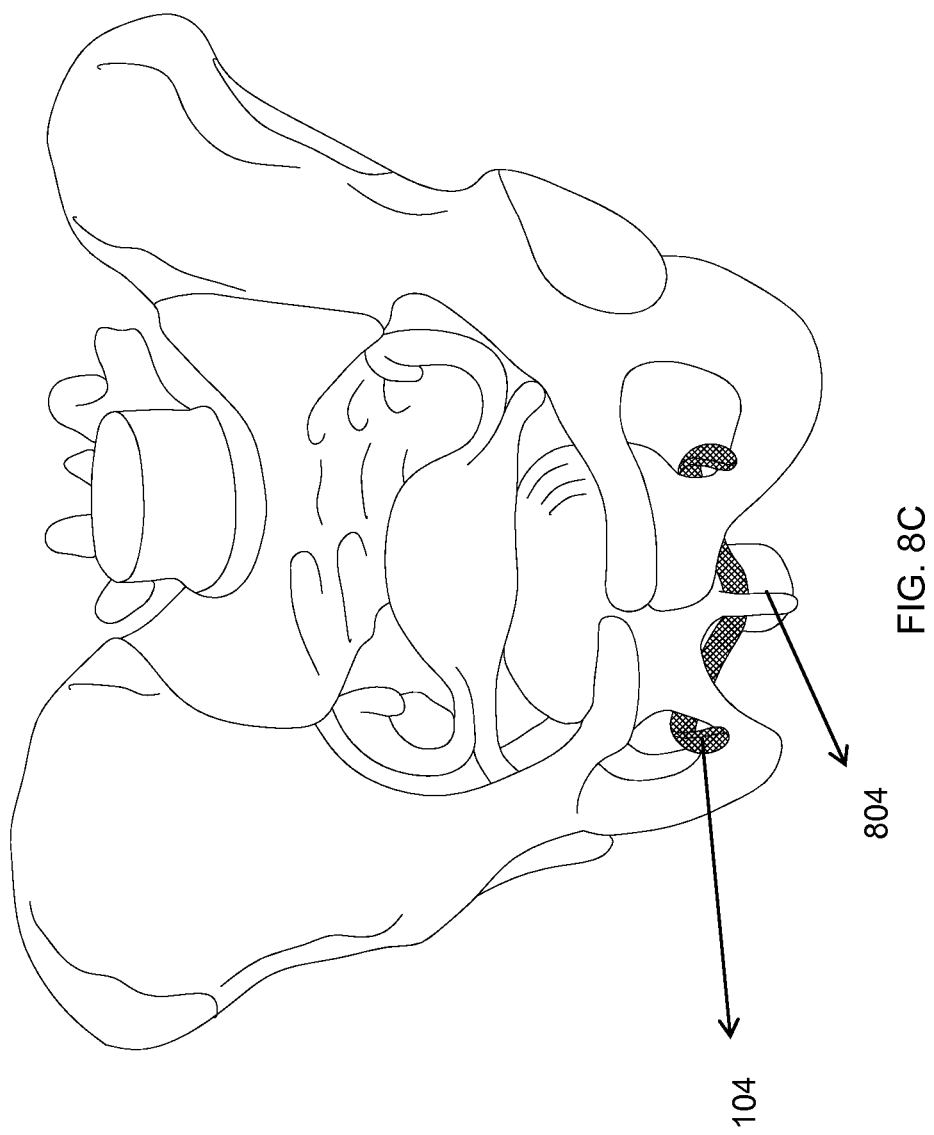

FIGS. 8A-8C illustrate delivery of a medical assembly for placement of an implant in a patient's body opening, in accordance with an embodiment of the present invention. The medical assembly 100 is being used hereafter to describe the placement procedure. However, other medical assemblies as described in conjunction with various figures above can also be employed in a similar manner.

FIG. 8A illustrates positioning of the medical assembly 100 inside a female body through a vaginal approach. The method of positioning the medical assembly 100 includes creating an incision in the vaginal space 202.

FIG. 8B illustrates positioning of the medical assembly 100 inside a female body through a retropubic approach. The retropubic approach positions the implant 104 under the urethra 804 in a U shape. The ends of the implant 104 are brought up behind a pubic bone 806 and out through skin incisions above the pubic bone 806, and coupled to tissues adjacent to the pubic bone. In some embodiments the implant 804 length is sized such that only the elongated member 802 exits the skin incision.

In some other embodiments the method can be achieved through a transburator approach as shown in FIG. 8C. In accordance with this approach, the implant 104 is passed under the urethra 804 and out through incisions in the groin compartment of the thigh (not shown in the diagram).

Figure 9:
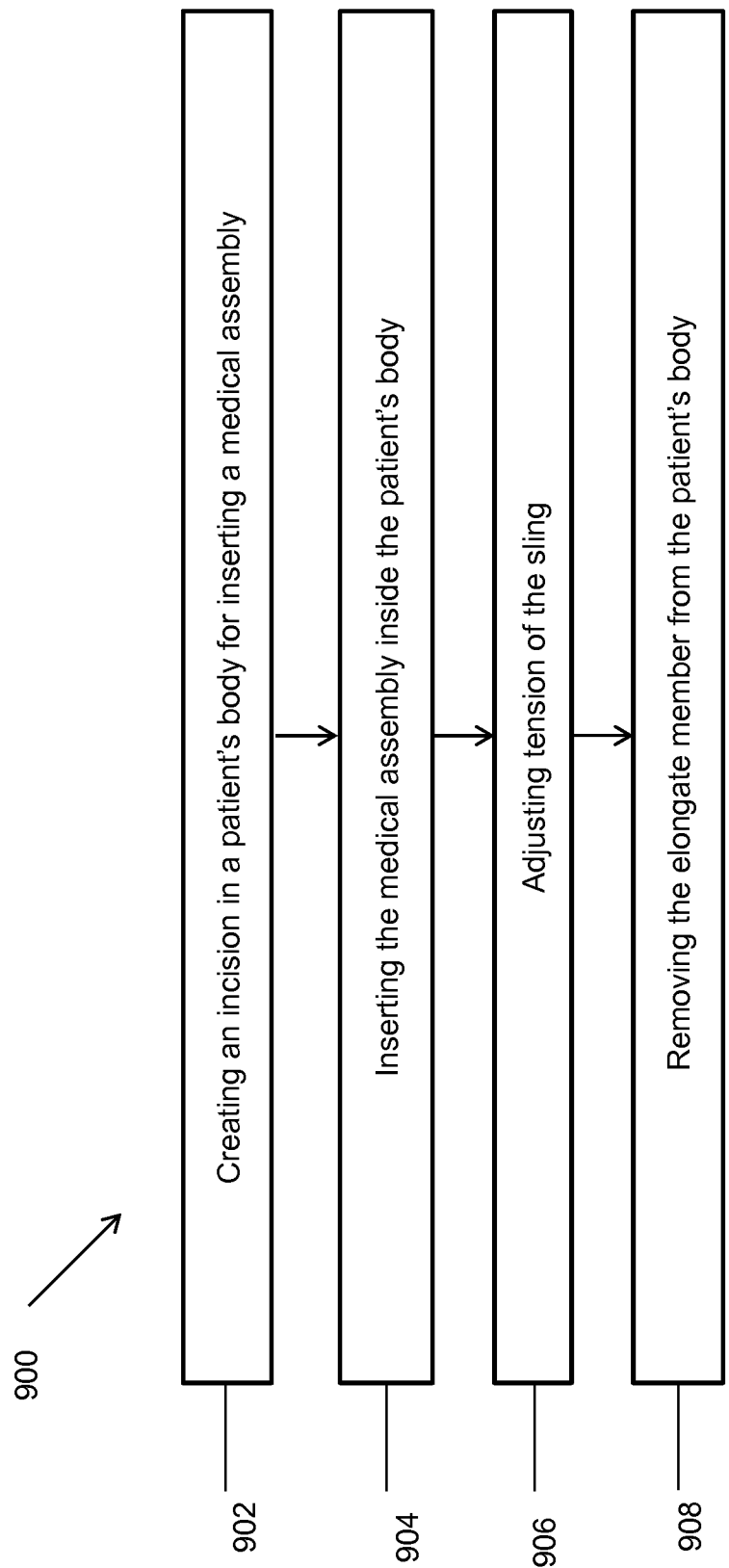
FIG. 9 illustrates a flowchart representing a method for delivery of a medical assembly in a patient's body, in accordance with an embodiment of the present invention.

FIG. 9 illustrates a flowchart representing a method 900 for delivery of the medical assembly 100 in a patient's body, in accordance with an embodiment of the present invention. Referring now to FIGS. 8A-9, a method for delivery of the medical assembly 100 in the patient's body is described.

The method 900 includes creating an incision in the patient's body for inserting the medical assembly 100 at step 902. The method of creating the incision and the location of the incision can vary based on the approach used as described above. The method further includes inserting the medical assembly 100 inside the patient's body at step 904. The medical assembly is inserted inside the patient's body such that the first surface contacts bodily tissues while the second surface does not make any contact with the bodily tissues. Subsequently, a tension of the implant 104 is adjusted to achieve a required level of support of the bodily tissues at step 906. While the elongate member 102 is still coupled, the implant 104 can be adjusted in either direction, thereby adjusting the tension of the implant 104. In accordance with various embodiments, the proximal end portion of the implant 104 is attached to a first bodily portion and the distal end portion of the implant 104 is attached to a second bodily portion. In some embodiments, the first bodily portion and the second bodily portion include tissues adjacent to the pubic bone.

Upon sufficiently tensioning the implant 104, the elongate member 102 is removed from the patient's body at step 908 such that the implant 104 stays at the desired bodily location to support the tissues. The elongate member 102 can be removed from the patient's body such that the elongate member 102 moves past the second surface of the implant 104 during removal. In some embodiments, the elongate member 102 and the coupling member 122 can be removed by cutting the loop and/or a portion of the implant 104 such as an implant leg anywhere along the length of the implant 104 external to the skin. Subsequently the cut portion is removed away from the skin. One of the cut ends of the loop similar to the loop shown in FIG. 3A as 322 will travel back into the body and unthread from the remaining portion of the implant leg as the elongate member 102 is pulled away from the body. In some embodiments, a contra lateral elongate member, if present, can be removed after or concurrently removed with the first elongate member 102 to place the implant 104.

In accordance with various embodiments, the elongate member 102 is separated from the implant 104 by decoupling the coupling member 122 prior to removal of the elongate member from the patient's body. The separating of the elongate member 102 from the implant 104 can be done by one of pulling, cutting, breaking, and melting the coupling member. In some embodiments, the elongate member 102 can be removed in a single piece by cutting the coupling member and/or the loop across the implant external to the body. During removal, the elongate member 102 travels back into the body and unthread from the remaining portion of the implant 104 as the elongate member 102 is pulled away from the body.

In certain embodiments, the coupling member can include tacks and threads (as described above in conjunction with FIG. 6G and 6H) that can be decoupled by various methods for separating the elongate member 102 from the implant 104. In accordance with these embodiments, the thread and a portion of the implant 104 such as implant legs can be cut to decouple and remove the elongate member 102. In some embodiments, end portions of the thread are left free ended after it is threaded through only the implant 104 in a tighter weave. In order to decouple the elongate member 102 from the implant 104, the thread and the implant 104 can be cut above an implant surface. The cut thread is then pulled out from the body unthreading the elongate member 102 and the implant 104. The tacks can be decoupled by breaking at a given load as the elongate member 102 and the implant 104 are pulled apart.

In some embodiments (as shown in FIG. 6B-6D), the thread can be decoupled in a manner similar to that described above. Since the implant 104 is not tacked to the elongate member 102 in accordance with these embodiments, there is no requirement of cutting the implant 104.

In some embodiments, (as shown in FIG. 6A), the thread can be decoupled in a similar manner as described above. However, in certain embodiments, if the thread extends to the contra lateral implant the thread is cut on both sides to release the elongate member 102. The cut thread can be removed through the midline incision, for example.

In some embodiments (as shown in FIG. 6E), the coupling member can be decoupled to release the elongate member 102 without being cut. In these embodiments, the thread that is configured to associate the elongate member 102 to the implant 104 is a separate thread than the thread used for the delivery device loop. The thread passes in and out of the elongate member 102 and the implant 104 in an upside down U pattern. In order to decouple and remove the elongate member 102, the upside down U pattern is pulled away from the body to withdraw the thread from the elongate member 102 and the implant 104. Once the thread is removed, the elongate member 102 is pulled away from the body.

In accordance with some other embodiments, the coupling member may include only tacks as shown in FIG. 6F. The tacks can be decoupled in a manner similar to described above by breaking at a given load as the elongate member 102 and the implant 104 are pulled apart.

Figure 2D:
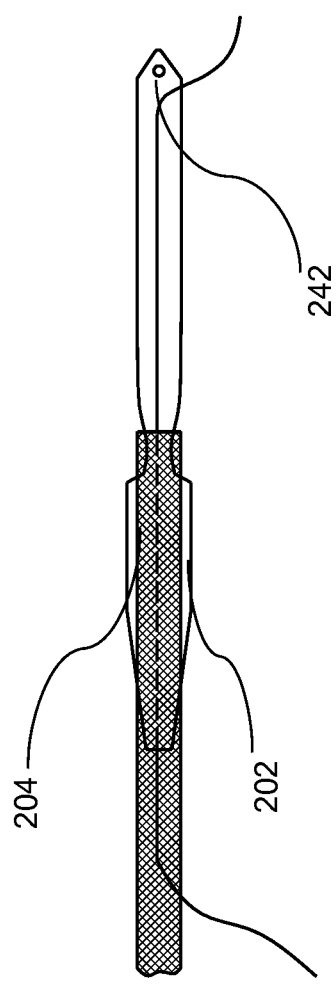
Figure 2:
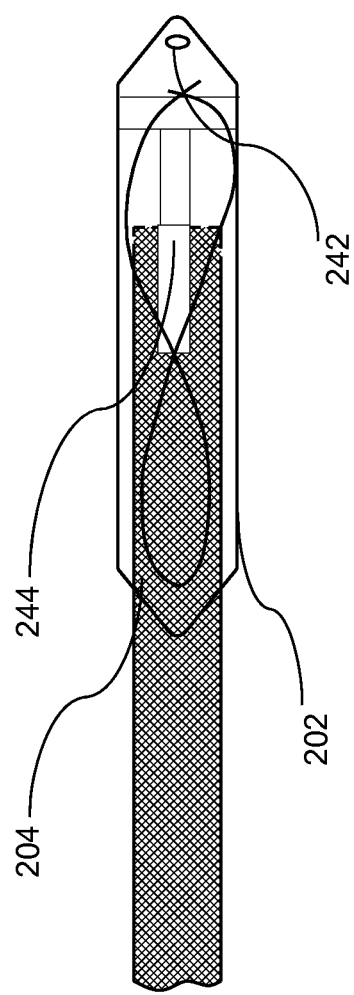
Figure 2:
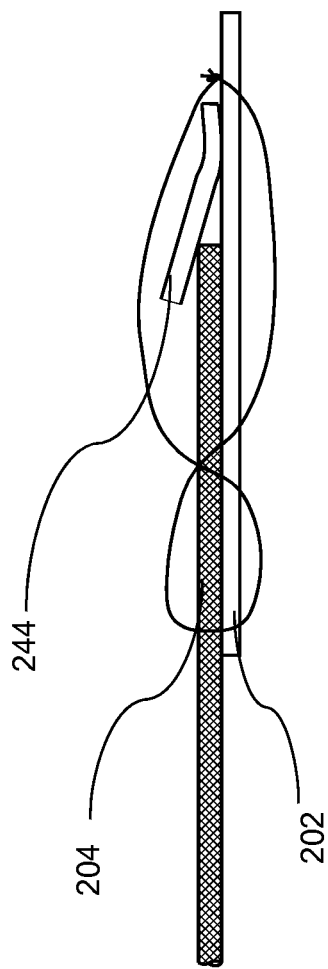

In accordance with some other embodiments and in conjunction with FIGS. 2C and 2D, the coupling member 232 can include a thread such that the thread is free at both ends and not secured to the elongate member 202 and or the implant 204. In an embodiment, the thread can be removed through the mid line incision. In another embodiment, the thread can be removed through the skin incision during an incontinence procedure. It is to be understood that the elongate member 202 can be removed in either direction after the thread has been removed. The tapered proximal end portion 206 of the elongate member 202 can be gripped by the operator to adjust the tension of the implant 204 without clamping onto the implant 204 itself as clamping to the implant 204 can cause damage to the implant 204. The end portions of the thread can be secured to the elongate member 202, the implant 204, or be an extension or part of another portion of the thread. This may require additional cutting of the thread for release.

In some embodiments, the end portions of the thread can be extended to the contra lateral side such that the thread at both sides can be removed by pulling the thread through the midline incision. It should also be understood that the elongate member 202 can be extended to the contra lateral side such that a single pull through the midline incision can remove the elongate member 202 from both sides. The extended elongate member 202 can also be cut via the midline incision to release the elongated member 202 on each side through the skin incision or through the midline incision.

In accordance with some embodiments, the implant 104 can be trimmed right below skin level after removal of the elongate member 102.

In accordance with the embodiments presented above for describing the method steps, an implant with a single mesh strip is employed for exemplary purposes. However, in accordance with various other embodiments, different types of implants can be used. For example, in an embodiment, the implant can include a support member and a plurality of arms extending from the support member and configured to be tied to different bodily locations within the patient's body. Further, each or some of the arms may be coupled to a separate elongate member similar to the elongate member describe above. In such embodiments, the method may include placing of the implant with the plurality of arms inside the patient's body, adjusting tension of each of the plurality of arms, and removing all the coupling members associated with each of the arms to lock and fix the arms at the desired location.

The incision can finally be closed using a suture or any other technique after the elongate member(s) is/are removed from the patient's body.

The above method focuses placement of the implant inside a female patient. However, it must be appreciated that the device can be used for a male patient.

In accordance with some or all of the embodiments above, the width of the implant is lesser than the width of the elongate member. Therefore, the elongate member prevents the implant from engaging surrounding body tissues as it is delivered and adjusted in either directions to a precise implant tension underneath the urethra or any other location for support. This assists in accurate tensioning adjustment of the implant.

In some embodiments, a medical assembly includes an elongate member and an implant. The elongate member has a proximal end portion and a distal end portion with a tapered tip. The tapered tip is configured to slide through a bodily tissue. The elongate member has a first width across at least a portion of the elongate member. The implant has a first surface and a second surface. The implant is coupled to the elongate member such that a portion of the first surface of the implant is overlaid over a portion of the elongate member while the second surface faces opposite to the elongate member and is configured to contact the bodily tissue while being inserted. The implant has a second width. The second width being smaller than the first width of the elongate member.

In some embodiments, the tapered tip includes folded edges of the distal end portion. In some embodiments, the tapered tip includes a taper-cut at the distal end portion. In some embodiments, the lumen is formed by folded edges at the distal end portion of the elongate member. In some embodiments, the lumen is formed by a removable dilator coupled to the distal end portion of the elongate member.

In some embodiments, the elongate member and the implant are formed of a synthetic material. In some embodiments, the synthetic material is a polymer. In some embodiments, the lumen is configured to be coupled to a delivery device. In some embodiments, the delivery device is a surgical needle.

In some embodiments, the assembly includes a coupling member. The coupling member is configured to couple the elongate member and the implant. In some embodiments, the coupling member is at least one selected from the group consisting of a thread, a tack, a skewer, a knot, a tuck and a tie.

In some embodiments, the assembly includes a loop at the distal end portion of the elongate member configured to form a connection between a delivery device and the lumen. In some embodiments, the loop extends along a portion of the elongate member and the implant to form a coupling member configured to couple at least a portion of the implant with the elongate member. In some embodiments, the elongate member is a first elongate member such that a first portion of the implant is coupled to the first elongate member. The medical assembly includes a second elongate member such that a second portion of the implant is coupled to the second elongate member.

In some embodiments, a method for treatment of a pelvic floor disorder in a patient's body, the method includes creating an incision in the patient's body for inserting a medical assembly, the medical assembly including an elongate member having a proximal end portion and a distal end portion with a tapering tip, the elongate member having a first width across at least a portion of the elongate member, and an implant having a first surface and a second surface, the implant being coupled to the elongate member such that a portion of the first surface of the implant is overlaid over a portion of the elongate member, wherein the implant has a second width, the second width being smaller than the first width of the elongate member; inserting the medical assembly inside the patient's body such that the first surface contacts bodily tissues during insertion; adjusting tension of the implant; and removing the elongate member from the patient's body such that the elongate member moves past the second surface of the implant during removal.

In some embodiments, the method includes separating the elongate member and the implant by decoupling a coupling member. In some embodiments, the coupling member is at least one selected from a group consisting of a thread, a tack, a skewer, a knot, a tuck and a tie. In some embodiments, the separating of the elongate member from the implant is done by at least one of pulling, cutting, breaking, and melting. In some embodiments, the attaching a proximal end portion of the implant to a first bodily portion and a distal end portion of the implant to a second bodily portion. In some embodiments, the first bodily portion and the second bodily portion include tissues adjacent to a pubic bone.

In some embodiments, the implant includes a support member and a plurality of arms extending from the support member. Each of the plurality of arms is configured to be coupled to a coupling member. The method further includes placing the plurality of arms within the patient's body, adjusting tension of the plurality of arms, and removing the coupling member associated with each of the arms. In some embodiments, the method includes closing the incision.

While the invention has been disclosed in connection with the some embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical assembly comprising:
   an elongate member having a proximal end portion and a distal end portion with a tapered tip, the tapered tip defining a lumen, the proximal end portion having a tapered portion, the tapered tip configured to slide through a bodily tissue, the elongate member having a width across at least a portion of the elongate member, the elongate member having a first surface and a second surface opposite to the first surface, the first surface being disposed in a different plane than the second surface;
   an implant having a proximal end portion and a distal end portion with a length extending between the proximal end portion and the distal end portion, the implant having a width defined between two longitudinal edges of the implant, the implant having a first surface and a second surface, the second surface of the implant being separated from the first surface of the implant by a thickness of the implant, the second surface of the implant being opposite to the first surface of the implant, the first surface of the implant being disposed in a different plane than the second surface of the implant, the first surface of the implant being coupled to the first surface of the elongate member outside the lumen, the second surface of the implant being configured to contact the bodily tissue when inserted into a body of a patient, the elongate member not contacting any portion of the second surface of the implant, the width of the implant being smaller than the width of the elongate member, the first surface of the implant being disposed between the second surface of the elongate member and the second surface of the implant; and
   a coupling member configured to couple the elongate member and the implant, the coupling member including a suture, the suture being threaded in and out of the elongate member and the implant,
   the suture forming a loop at the distal end portion of the elongate member, the loop configured to be coupled to a delivery device.

2. The medical assembly of claim 1, wherein the tapered tip includes folded edges of the distal end portion of the elongate member.

3. The medical assembly of claim 1, wherein the tapered tip includes a taper-cut at the distal end portion of the elongate member.

4. The medical assembly of claim 1, wherein the lumen is formed by folded edges at the distal end portion of the elongate member.

5. The medical assembly of claim 1, wherein the distal end portion of the implant includes a tanged section having tangs configured to engage tissue to secure the implant, and the proximal end portion of the implant includes a de-tanged section that is devoid of tangs to avoid mesh irritation upon placement of the implant underneath a urethra.

6. The medical assembly of claim 1, wherein the width of the implant is the same along the length of the implant.

7. The medical assembly of claim 1, wherein the elongate member has a length longer than a length of the implant.

8. The medical assembly of claim 1, wherein the elongate member and the implant include a non-woven polymeric material.

9. The medical assembly of claim 1, wherein the delivery device is a surgical needle defining a slot configured to engage with the loop.

10. The medical assembly of claim 1, wherein the suture extends across a length of the implant.

11. The medical assembly of claim 1 further comprising a flap having a first end portion and a second end portion, the first end portion of the flap being coupled to the distal end portion of the elongate member, the flap configured to protect a leading edge of the implant from engaging with tissue.

12. The medical assembly of claim 11, wherein the second end portion of the flap is not coupled to any portion of the elongate member.

13. The medical assembly of claim 1, wherein the elongate member is a first elongate member such that a first portion of the implant is coupled to the first elongate member, the medical assembly further comprising a second elongate member such that a second portion of the implant is coupled to the second elongate member.

14. A method for treatment of a pelvic floor disorder in a patient's body, the method comprising:

creating an incision in the patient's body for inserting a medical assembly, the medical assembly including an elongate member having a proximal end portion and a distal end portion with a tapering tip, the elongate member having a first surface and a second surface opposite to the first surface, the first surface being disposed in a different plane than the second surface, the tapered tip defining a lumen, the elongate member having a width across at least a portion of the elongate member, the medical assembly including an implant having a first surface and a second surface, the second surface of the implant being separated from the first surface of the implant by a thickness of the implant, the first surface of the implant being disposed in a different plane than the second surface of the implant, the first surface of the implant being coupled to the first surface of the elongate member outside the lumen, the first surface of the implant being coupled to a portion of the elongate member that is devoid of a lumen, the elongate member not contacting any portion of the second surface of the implant, the width of the elongate member being larger than a width of the implant, the first surface of the implant being disposed between the second surface of the elongate member and the second surface of the implant, the medical assembly including a coupling member that couples the elongate member and the implant, the coupling member including a suture, the suture being threaded in and out of the elongate member and the implant, the suture forming a loop at the distal end portion of the elongate member, the loop being coupled to a delivery device, the medical assembly including a flap having a first end portion and a second end portion, the first end portion of the flap being coupled to the distal end portion of the elongate member;

inserting the medical assembly inside the patient's body using the delivery device such that the second surface of the implant contacts bodily tissues during insertion, the flap protecting a leading edge of the implant when the medical device is inserted inside the patient's body;

adjusting tension of the implant; and removing the elongate member from the patient's body such that the elongate member is decoupled from the first surface of the implant, wherein the removing includes cutting the loop to create cut ends, and one of the cut ends of the loop enter into the patient's body and unthread the implant as the elongate member is pulled away from the patient's body.

15. The method of claim 14, wherein the suture extends across a length of the implant.

16. The method of claim 14, wherein the delivery device includes a slot that engages with the loop.

17. The method of claim 14 further comprising attaching a proximal end portion of the implant to a first bodily portion and a distal end portion of the implant to a second bodily portion.

18. The method of claim 17, wherein the first bodily portion and the second bodily portion include tissues adjacent to a pubic bone.

* * * * *